(12) United States Patent
Lampropoulos et al.

(10) Patent No.: US 11,109,904 B2
(45) Date of Patent: Sep. 7, 2021

(54) DEVICES FOR PERFORMING A MEDICAL PROCEDURE WITHIN AN APPROPRIATE INTERVAL AND RELATED SYSTEMS AND METHODS

(71) Applicant: DFine, Inc., South Jordan, UT (US)

(72) Inventors: Fred Lampropoulos, Salt Lake City, UT (US); Jim Mottola, West Jordan, UT (US); Nate Shirley, Pleasant Grove, UT (US); Blaine Johnson, Riverton, UT (US)

(73) Assignee: DFine, Inc., South Jordan, UT (US)

( * ) Notice: Subject to any disclaimer, the term of this patent is extended or adjusted under 35 U.S.C. 154(b) by 200 days.

(21) Appl. No.: 15/290,784

(22) Filed: Oct. 11, 2016

(65) Prior Publication Data

US 2017/0100178 A1    Apr. 13, 2017

Related U.S. Application Data

(60) Provisional application No. 62/240,061, filed on Oct. 12, 2015.

(51) Int. Cl.
*A61B 17/88* (2006.01)
*A61B 90/00* (2016.01)
*A61L 27/16* (2006.01)

(52) U.S. Cl.
CPC ...... *A61B 17/8805* (2013.01); *A61B 17/8833* (2013.01); *A61B 90/06* (2016.02); *A61L 27/16* (2013.01); *A61B 2017/883* (2013.01); *A61L 2400/06* (2013.01)

(58) Field of Classification Search
CPC ............................. A61B 17/8805–2017/8838
See application file for complete search history.

(56) References Cited

U.S. PATENT DOCUMENTS

| | | | |
|---|---|---|---|
| 4,854,716 A * | 8/1989 | Ziemann | B01F 15/00253 366/139 |
| 5,108,404 A | 4/1992 | Scholten et al. | |
| 5,354,287 A * | 10/1994 | Wacks | A61M 5/24 128/DIG. 1 |
| 8,487,021 B2 * | 7/2013 | Truckai | A61K 31/78 523/211 |
| 9,918,767 B2 * | 3/2018 | Globerman | A61B 17/8836 |

(Continued)

FOREIGN PATENT DOCUMENTS

| | | | |
|---|---|---|---|
| EP | 1834609 | 9/2007 | |
| EP | 1834609 A2 * | 9/2007 | ......... A61B 17/8833 |
| WO | 2006062939 | 6/2006 | |

OTHER PUBLICATIONS

International Search Report and Written Opinion dated Jan. 11, 2017 for PCT/UC2016056431.
European Search Report dated May 13, 2019 for EP16856035.7.

*Primary Examiner* — Zade Coley
(74) *Attorney, Agent, or Firm* — Stoel Rives LLP

(57) ABSTRACT

Systems and methods for indicating an interval in which a procedure (or sub-procedure) should be carried out are disclosed. Some systems and methods involve timing various sub-procedures and alerting a practitioner at the completion of a sub-procedure period. Some systems and methods include a sensor, such as a temperature sensor, that is used determine a window of time in which a variable-viscosity material is of suitable viscosity for delivery to a patient.

17 Claims, 17 Drawing Sheets

(56) References Cited

U.S. PATENT DOCUMENTS

| | | | | |
|---|---|---|---|---|
| 9,931,468 B1* | 4/2018 | Pacifico | ............ | B01F 15/00246 |
| 2005/0209602 A1* | 9/2005 | Bowman | ................. | A61F 2/441 |
| | | | | 606/90 |
| 2005/0245839 A1* | 11/2005 | Stivoric | ................. | G01K 1/024 |
| | | | | 600/549 |
| 2006/0074433 A1* | 4/2006 | McGill | ............. | A61B 17/8822 |
| | | | | 606/92 |
| 2006/0079905 A1* | 4/2006 | Beyar | ................ | A61B 17/7095 |
| | | | | 606/76 |
| 2007/0027230 A1* | 2/2007 | Beyar | ............... | B01F 15/00876 |
| | | | | 523/117 |
| 2009/0057168 A1* | 3/2009 | Smit | ................... | A61B 17/8833 |
| | | | | 206/221 |
| 2009/0062808 A1* | 3/2009 | Wolf, II | ............. | A61B 17/8822 |
| | | | | 606/93 |
| 2009/0093818 A1* | 4/2009 | Baroud | ................ | A61F 2/4601 |
| | | | | 606/93 |
| 2009/0198242 A1* | 8/2009 | Truckai | ............. | A61B 17/8822 |
| | | | | 606/93 |
| 2009/0247664 A1* | 10/2009 | Truckai | .................. | A61L 27/16 |
| | | | | 523/116 |
| 2014/0148866 A1* | 5/2014 | Globerman | ........ | A61B 17/8836 |
| | | | | 606/86 R |

* cited by examiner

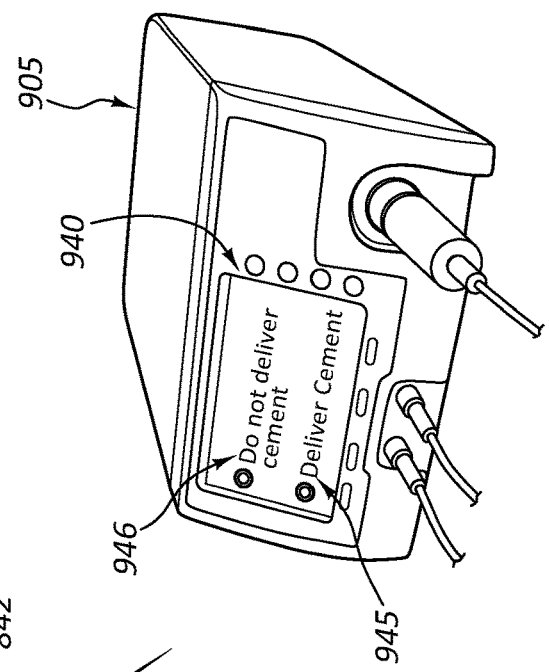
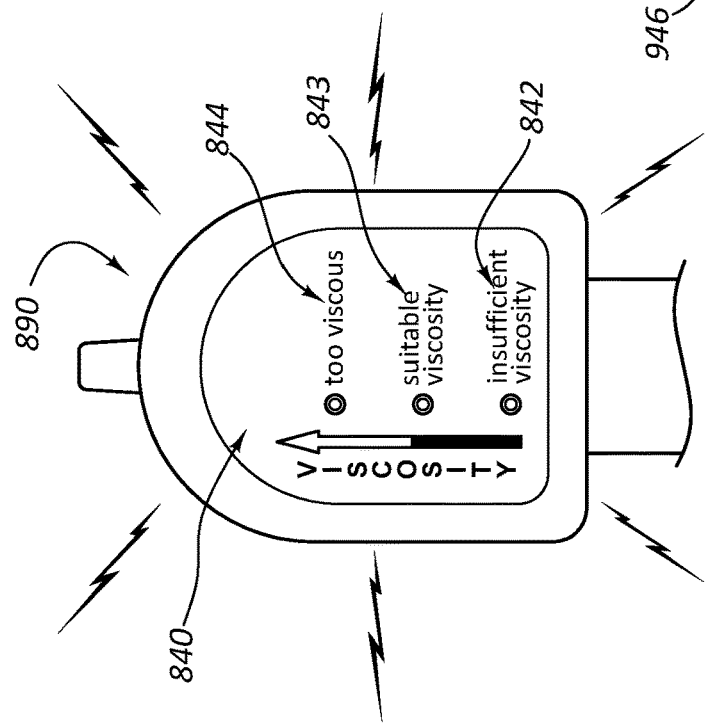
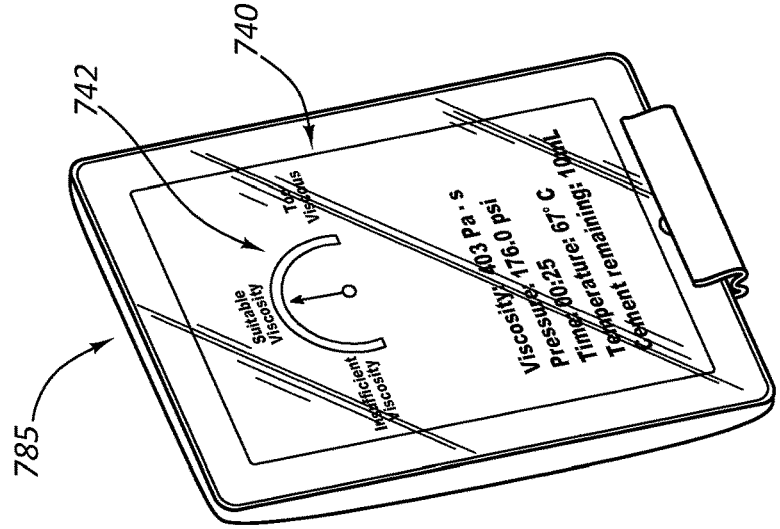
FIG. 19
FIG. 18
FIG. 17

DEVICES FOR PERFORMING A MEDICAL PROCEDURE WITHIN AN APPROPRIATE INTERVAL AND RELATED SYSTEMS AND METHODS

RELATED APPLICATIONS

This application claims priority to U.S. Provisional Application No. 62/240,061, filed on Oct. 12, 2015 and titled, "Methods and Apparatuses For Timing Medical Treatment Procedures," which is hereby incorporated by reference in its entirety.

TECHNICAL FIELD

The present disclosure relates generally to the field of medical devices and related systems and methods. More particularly, some embodiments relate to medical devices that identify an interval during which a medical procedure (or a step thereof) should occur.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 17 depicts a remote display for displaying indicia during a medical procedure.

FIG. 18 depicts another display for displaying indicia during a medical procedure.

FIG. 19 depicts still another display for displaying indicia during a medical procedure.

DETAILED DESCRIPTION

Figure 1:
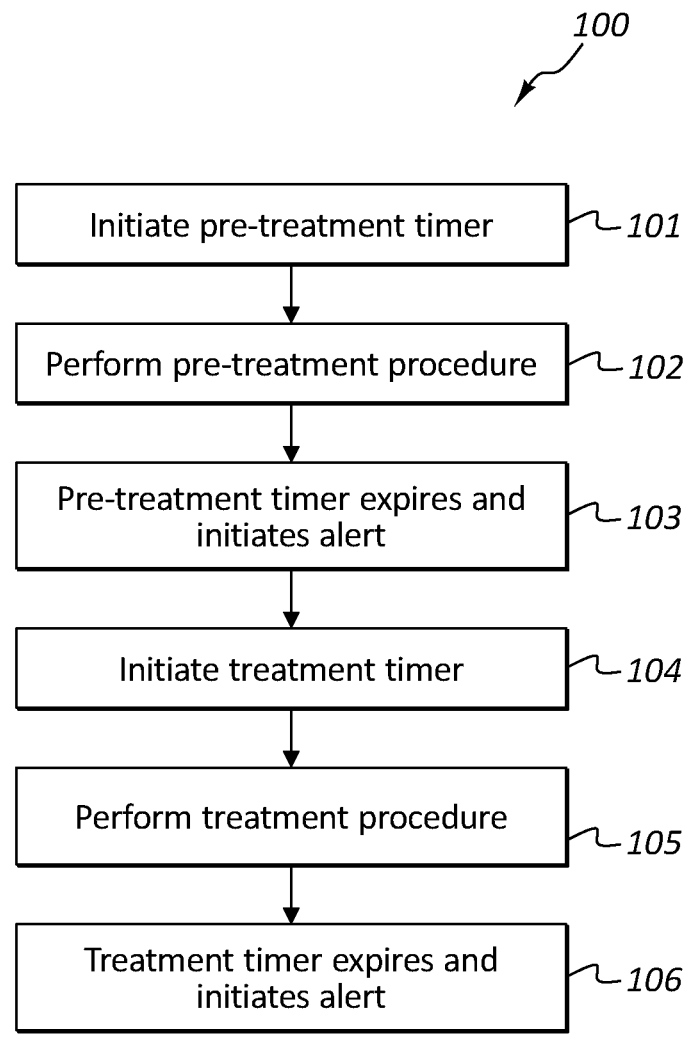
FIG. 1 is a flow chart of a method for timing a pre-treatment procedure and a treatment procedure.

In some medical procedures, one or more steps (or an entirety) of the medical procedure should (or preferably) occur within a particular time interval. Medical devices and systems described herein can aid a practitioner in carrying out one or more steps of a procedure within the desired interval.

For example, in some embodiments, a practitioner may be alerted to the completion of various intervals for carrying out particular sub-procedures. In some embodiments, such alerts may be provided by indicia that alert the practitioner of one or more interval boundary based solely on elapsed time. In other embodiments, the one or more indicia alert the practitioner of an interval boundary based, at least in part, on some other parameter. For example, in some embodiments, an interval boundary is determined, at least in part, based on input from a sensor, such as a temperature sensor.

As timing, including measuring time intervals for portions of a treatment, is a component of many medical procedures, appropriately tracking time elapsed during a treatment may directly correlate to the success of the procedure. As used herein, a treatment refers to any procedure or therapy, including treatments performed on a patient, such as medical procedures, dental procedures, and so forth. Sometimes, procedures are complex and comprise multiple smaller procedures or sub-procedures, each of which may have its own time constraints.

Kyphoplasty and vertebroplasty procedures may be divided into at least two sub-procedures. One such sub-procedure may be defined as a "pre-treatment procedure" and may occur prior to a second sub-procedure or a main "treatment procedure." The pre-treatment procedure may include preparation of a mixture (e.g., by combining ingredients, allowing the combined ingredients to react, or so forth). The treatment procedure may then make use of the prepared mixture; for example, the treatment procedure may include injection of the mixture into a vertebra of a patient. In some cases, the ingredients may be configured to mix, integrate, or react for a specified amount of time before the mixture is indicated as prepared for injection into the patient's vertebra. During the treatment procedure, a medical practitioner may then inject the mixture into the patient's vertebra to treat compression fractures and/or other related ailments.

Further, the treatment procedure may also be associated with time intervals. For example, in some instances the mixture will begin to cure or harden after the ingredients have been combined. Thus, the mixture may have a window of effective time for use in the treatment procedure. Accordingly, in some kyphoplasty or vertebroplasty procedures, a medical practitioner must be aware of time constraints to perform the procedure successfully.

Other sub-procedures involved in kyphoplasty or vertebroplasty are within the scope of this disclosure and may, in isolation or in combination with other sub-procedures, comprise the pre-treatment procedure and/or the treatment procedure. Exemplary other sub-procedures include: making an incision in the back of a patient through which the medical practitioner inserts a narrow tube, using fluoroscopy to guide the narrow tube to the fractured area of the patient's vertebra, using x-ray imaging to insert an inflatable device through the tube and into the vertebra, inflation of the inflatable device to elevate the fracture and create a cavity inside the vertebra, and removing the inflatable device to prepare for injection of the mixture.

Some procedures described herein are particularly suitable for delivery of a material that changes viscosity over time to patient. Stated differently, in some embodiments, a variable-viscosity material may be injected into a patient and then allowed to harden within the patient.

Kyphoplasty and vertebroplasty are also examples of a medical procedure that may involve the delivery of variable-viscosity material to a patient. For example, during a kyphoplasty or vertebroplasty procedure, a variable-viscosity material may be prepared by mixing one or more substances. Immediately after mixing, the variable-viscosity material may have a relatively low viscosity, thereby rendering the mixture unsuitable for delivery within a patient. In other words, due to the relatively low initial viscosity of the material, the mixture may initially be too "runny" for injection to a localized region within a patient. Over time, the mixture may increase in viscosity, thereby rendering the mixture of suitable viscosity for localized delivery into a patient. For example, when the variable-viscosity material (e.g., a cement) is of suitable viscosity, the variable-viscosity material may be injected into one or more damaged vertebrae of a patient. The variable-viscosity material may then be allowed to harden within the patient. The hardened material may strengthen and/or stabilize the vertebra(e). In this manner, compression fractures and other ailments may be treated.

If the variable-viscosity mixture is allowed to harden for an extended period of time before delivery into the patient, the mixture may become too viscous for its intended purpose. For example, the mixture may have insufficient flowability, thereby preventing the mixture from filling recesses in a vertebra. Mixtures that are too viscous may additionally or alternatively damage delivery equipment and/or require an inordinate amount of pressure to ensure delivery.

Thus, practitioners may benefit from devices and systems that are configured to help a practitioner determine when a substance is of suitable viscosity for delivery into a patient.

Some variable-viscosity materials increase in viscosity (i.e., harden) more quickly at high temperatures than at low temperatures. As the rate at which many variable-viscosity mixtures change viscosity (e.g., harden) is temperature-dependent, devices and systems may include one or more sensors that are designed to sense the ambient temperature and/or the temperature of the variable-viscosity mixture.

Additionally or alternatively, for variable-viscosity mixtures in which the rate of change in viscosity is pressure dependent, pressure sensors may be used to sense the pressure within a chamber that contains the variable-viscosity mixture. The data from the one or more sensors may be used to more accurately determine the current viscosity of the mixture and/or estimate when the variable-viscosity mixture will be (and/or will cease to be) of suitable viscosity for delivery to a patient.

Various other treatments (i.e., treatments that do not involve kyphoplasty or vertebroplasty) involving timing or the sequence of one or more events are likewise within the scope of this disclosure. Medical procedures, dental procedures, and other types of therapies may involve measurement of time intervals, including measurement of a time interval for a pre-treatment procedure and measurement of a time interval for a treatment procedure.

Angioplasty is another exemplary procedure in which timing may be monitored. During an angioplasty procedure, sub-procedures may comprise one or more of: administering anesthesia, accessing the vasculature of a patient, inserting a catheter through the tubular member to a endovascular lumen in a patient, injecting radiopaque materials into the endovascular lumen for radiographic viewing to identify a blockage in the endovascular lumen, inserting an inflatable device into the endovascular lumen of a patient, and inflating an inflatable device with the endovascular lumen of a patient to unblock the endovascular lumen. Inflation of the inflatable device inside the vasculature of the patient may tend to block blood flow. Thus, a practitioner may desire to limit the amount of time the inflatable device is inflated during the treatment. For example, in some instances it may be unsafe for an inflatable device to remain inflated for too long, as prolonged inflation may lead to a decrease in blood flow and damage to the patient.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any connection or coupling between two or more entities. Two components may be coupled to each other even though they are not in direct contact with each other. For example, two components may be coupled to each other through an intermediate component. The phrase "fluid communication" is used in its ordinary sense, and is broad enough to refer to arrangements in which a fluid (e.g., a gas or a liquid) can flow from one element to another element when the elements are in fluid communication with each other.

The terms "proximal" and "distal" are opposite directional terms. For example, the distal end of a device or component is the end of the component that is furthest from the practitioner during ordinary use. The proximal end refers to the opposite end, or the end nearest the practitioner during ordinary use. A "variable-viscosity" substance, material, or mixture is a substance, material, or mixture that increases in viscosity over time. A "delivery period" is a period of time that is demarcated by one or more indicia, wherein the one or more indicia indicate that a variable-viscosity material or mixture is of suitable viscosity for delivery to a patient during the indicated period of time. Conversely, a "non-delivery period" is a period of time that is demarcated by one or more indicia, wherein the one or more indicia indicate that a variable-viscosity material or mixture is not (or may not be) of suitable viscosity for delivery to a patient.

FIG. 1 is a flow chart illustrating a method 100 of performing a treatment or therapy comprising at least a pre-treatment procedure and a treatment procedure. It is within the scope of this disclosure to perform any subset of the listed steps in any suitable order. Likewise, with any subsequent embodiments or methods disclosed herein, it is within the scope of this disclosure to perform any subset of the listed steps in any suitable order.

In the illustrated embodiment of the method 100, the first step 101 is designated as "Initiate pre-treatment timer." A pre-treatment timer may be initiated by user input, for example through triggering an actuator such as a button or other input, with a force, including depressing an actuator with a compression force. In other embodiments of the method 100, the pre-treatment timer may be initiated by receiving data from a sensor configured to measure any input, such as pressure, sound, touch, and/or vibration. In other embodiments of the method 100, the pre-treatment timer may be initiated by one or more of an audible command, a visible command, a touch sensor, a command from a remote computing device, or some other input method.

The pre-treatment timer can measure an event by various methods, for example by counting down time or counting up time. In some embodiments of the method 100, the pre-treatment timer is set to measure a time interval of less than five minutes, including intervals of less than three minutes, less than two minutes, between one minute and three minutes, or between one and a half minutes and two and a half minutes. In some embodiments of the method 100, the pre-treatment timer is pre-set to measure a set time interval. In other embodiments of the method 100, the pre-treatment timer is programmable for any time interval. In some such embodiments, a practitioner may set the time interval prior to beginning the procedure as part of the step 101 of initiating the pre-treatment timer.

The second step 102 of the illustrated method is designated as "Perform pre-treatment procedure." A pre-treatment procedure may be any sub-procedure, portion of a procedure, or step of a more extensive procedure. For example, a pre-treatment procedure may be an initial sub-procedure performed in preparation for a treatment procedure. In other embodiments, a pre-treatment procedure may be one or more of any sub-procedure performed in preparation for a treatment procedure. Exemplary pre-treatment procedures may include one or more of (1) combining ingredients to be used in a treatment procedure, (2) applying or injecting anesthetics to a patient, (3) sterilizing tools or other materials to be used in a treatment procedure, (4) accessing a part of a patient's body in preparation for a treatment procedure, (5) preparing surgical tools to be used in a treatment procedure, (6) curing materials to be used in a treatment procedure, (7) permitting a reaction to occur prior to a treatment procedure, (8) any of the sub-procedures disclosed herein, and (9) any similar procedure performed prior to another sub-procedure or treatment procedure.

Any pre-treatment procedure, including the examples outlined above, may thus be timed by the pre-treatment timer. The time interval measured by the pre-treatment timer may correlate to one or more variables of the pre-treatment procedure, such as the time indicated for materials to mix or react, anesthesia to take effect, an area or tool to be sterilized, and so forth.

The third step 103 indicated in the illustrated method 100 is designated as "Pre-treatment timer expires and initiates alert." When the pre-treatment timer on the timing mechanism expires or completes a cycle, for example by completing a countdown to zero or a count up to a specified time, the timing mechanism may initiate a pre-treatment alert. The pre-treatment alert may comprise any indicia conveyable to a practitioner that the pre-treatment time interval has been reached. Examples of such indicia are further outlined below.

The pre-treatment alert indicia may be proximal to, or remote from, the timing mechanism. The pre-treatment alert may be configured to notify a medical professional that the time interval has been reached. The pre-treatment alert may be in the form of, for example, visible indicia such as lights, colors, text, and so forth or non-visible indicia such as sounds or vibrations. Combinations of such indicia are also within the scope of this disclosure. In some embodiments of the method 100, the pre-treatment alert can provide information in addition to the status of the time interval, including, but not limited to, one or more of: time remaining until termination of the timer, time passed since expiration of the timer, time remaining until termination of the pre-treatment alert, and time remaining until the beginning of a new timer.

The pre-treatment alert and/or any associated indicia may be configured to communicate additional information in addition to the expiration of the pre-treatment time interval. A pre-treatment alert in the form of a light may be a flashing light, a solid light, and patterns or combinations of light pulses. In some embodiments of the method 100, a flashing or pulsed light indicia may convey information in addition to the termination of the timer. For example, the number or pace of the light pulses may correlate to the status of the pre-treatment procedure. Analogously, in some embodiments of the method 100, a pre-treatment alert in the form of a sound may convey information in addition to the termination of the timer by changing volume or sound pattern to indicate the additional information. In some embodiments of the method 100, a pre-treatment alert in the form of a vibration may convey information in addition to the termination of the timer via vibration pattern or strength, for example. Examples of such additional information include a count of the number of procedures performed, an indication of the beginning of some other portion of the procedure, or information about the physical characteristics of a compound or mixture, such as temperature or viscosity.

The fourth step 104 of the method 100 is designated as "Initiate treatment timer." It will be appreciated by one of skill in the art having the benefit of this disclosure, that disclosure relating to the initiation, measurement, alerts, and other characteristics of the pre-treatment timer may apply analogously to the treatment timer and vice versa. For example, in some embodiments of the method 100, the treatment timer may be initiated using any one or more of the methods disclosed for initiating the pre-treatment timer.

Still further, in some embodiments of the method 100, the treatment timer may be automatically initiated by the timing mechanism after initiating the pre-treatment alert. In some embodiments of the method 100, the timing mechanism automatically initiates the treatment timer immediately after termination of the pre-treatment alert. In other embodiments of the method 100, the timing mechanism automatically initiates the treatment timer after a period of time has passed since the termination of the pre-treatment timer. In some embodiments of the method 100, the treatment timer counts down. In other embodiments of the method 100, the treatment timer counts up. In some instances, the treatment timer is set to measure a time interval between 25 and 35 minutes, a time interval between 20 and 40 minutes, and intervals of less than 60 minutes, 50 minutes, 40 minutes, 30 minutes, 20 minutes, or 10 minutes. In some embodiments of the method 100, the interval length of the treatment timer is pre-set. In other embodiments of the method 100, the treatment timer is programmable by a user.

The fifth step 105 of the illustrated method 100 is indicated as "Perform treatment procedure." The treatment procedure can be any medical procedure, therapy, treatment, or portion thereof, including, but not limited to (1) performing surgery, (2) casting a broken bone, (3) performing a dental procedure, (4) performing an examination with a scope, (5) performing an angiography, (6) performing a kyphoplasty or vertebroplasty procedure, (7) any sub-procedures of the preceding, and (8) any sub-procedures disclosed herein.

As discussed above, and analogous to the step 102 of performing the pre-treatment procedure, the step 105 of performing the treatment procedure may include one or more steps or processes wherein a measured time interval is related to the procedure. As further detailed below, various portions of a treatment procedure may relate to a time interval. For example, a drug used during the treatment procedure may correlate to a time interval of efficacy, a compound or mixture used in the treatment procedure may have a time window of viability for use in the procedure, or portions of the procedure may need to be completed within a time window to avoid unwanted trauma to the patient.

The sixth step 106 of the illustrated method 100 is indicated as "Treatment timer expires and initiates alert." When the treatment timer on the timing mechanism indicates expiration of the treatment time interval (or "terminates") by, for example, completing a countdown to zero or a count up to a specified time, the timing mechanism may initiate a treatment alert. The treatment alert may be configured to notify a medical professional that the treatment timer interval has expired. The treatment alert may have any one or more of the characteristics or indicia of the pre-treatment alert disclosed above.

Other embodiments of methods of performing a therapy or treatment such as a surgery comprising a pre-treatment procedure and a treatment procedure may comprise any one or more of the steps of method 100 described herein. Again, methods comprising any subset or combination of the illustrated procedure, including repetition of any of the illustrated steps, are within the scope of this disclosure. Still further, it is within the scope of this disclosure to perform the steps in any sequence or pattern. Thus, in some embodiments, the steps of the method 100, or a subset or portion thereof, may be performed in an order different from that described in connection with method 100.

Kyphoplasty and vertebroplasty procedures are examples of a therapy or treatment within the scope of the outlined method 100. During a kyphoplasty or vertebroplasty procedure, for example, a practitioner may actuate or initiate a pre-treatment timer, step 101. Initiation of the pre-treatment timer 101 may correlate to mixing of ingredients to form a mixture for use during the procedure. For example, the procedure may include the use of a cement or other mixture produced by mixing two or more ingredients and allowing the mixture to react for a first time interval. This first time interval may thus be measured by the pre-treatment timer.

The step of performing the pre-treatment procedure 102 may include mixing of the ingredients of the mixture and allowing the mixture to react. It is within the scope of this disclosure for a practitioner to initially mix the ingredients prior to initiation of the pre-treatment timer, then initiate the pre-treatment timer, such that the time interval correlates to a minimum amount of time for the ingredients to react. It is also within the scope of this disclosure for the practitioner to initiate the pre-treatment timer, and then mix the ingredients such that the pre-treatment time interval correlates to the time needed to mix the ingredients and allow them to react.

With reference to the exemplary kyphoplasty or vertebroplasty procedure, step 103 of the illustrated procedure, or expiration of the pre-treatment timer and initiation of the pre-treatment alert, may serve to notify the practitioner that the pre-treatment time interval has elapsed and the mixture is ready for use in a procedure. Again, any type of indicia for the pre-treatment alarm is within the scope of this disclosure, including an audible tone or visual indication on the timing device itself. In some kyphoplasty or vertebroplasty procedures, the time interval associated with preparing a cement mixture may be from one minute to three minutes, including time intervals of about two minutes. Again, this time interval may be pre-set or set by the practitioner during the procedure.

The next illustrated step 104 or initiation of a treatment timer, may be directly performed by the practitioner through an actuator, or may commence automatically upon the elapse of the pre-treatment time interval. In some kyphoplasty or vertebroplasty procedures, the mixture may have an effective time window of between 20 minutes and 40 minutes, including 30 minutes. Thus, for some kyphoplasty or vertebroplasty procedures, the pre-treatment time interval may measure an elapsed time of two minutes, whereupon an alert is issued, such as an audible beep. The treatment timer may then automatically commence and measure an elapsed time relating to a time window for the use of the mixture in the kyphoplasty or vertebroplasty procedure.

The practitioner may then perform the treatment procedure, step 105, by utilizing the cement or mixture to reinforce a patient's vertebra. The treatment timer may measure an elapsed time wherein the cement or mixture has a hardness, viscosity, or other property within a range indicated for injection into a patient. At the end of the treatment timer window, the mixture may be partially cured such that the cement is no longer indicated for such use. For example, the cement may be partially cured and too viscous for injection.

Step 106, expiration of the treatment time and initiation of the treatment alert, may thus signal to the practitioner to stop injecting or otherwise manipulating the cement or mixture as part of the kyphoplasty or vertebroplasty procedure. Like the pre-treatment alert, various indicia may indicate that the treatment window has elapsed. In some instances, the treatment alert may be identical to the pre-treatment alert, while in others instances, it may differ. For example, the pre-treatment alert may correspond to a single audible tone, while the treatment alert comprises multiple audible tones in succession.

Again, this outlined kyphoplasty/vertebroplasty procedure is exemplary in nature, illustrating one potential procedure within the scope of the procedure 100 illustrated in FIG. 1.

Timing of various procedures is within the scope of this disclosure. For example, any procedure wherein one, two, three, or more time intervals are measured during the procedure is within the scope of this disclosure. The illustrated method 100 includes an initiation and expiration of a pre-treatment timer 101, 103 and a treatment timer 104, 106. In other embodiments, three or more timers may be utilized in succession to measure additional parts of a treatment and to issue alerts at various time intervals.

Furthermore, as used herein, "timers" such as the pre-treatment timer and the treatment timer refer to a feature or capacity of a device or timing mechanism that sets and/or tracks a time interval. Thus, a single physical device or timing mechanism, such as a single circuit board having a single display or other output, may be configured to track the time intervals of multiple procedures, alone or in succession. Thus, one physical instrument or timing mechanism may comprise two, three, four, or more "timers."

Figure 2:
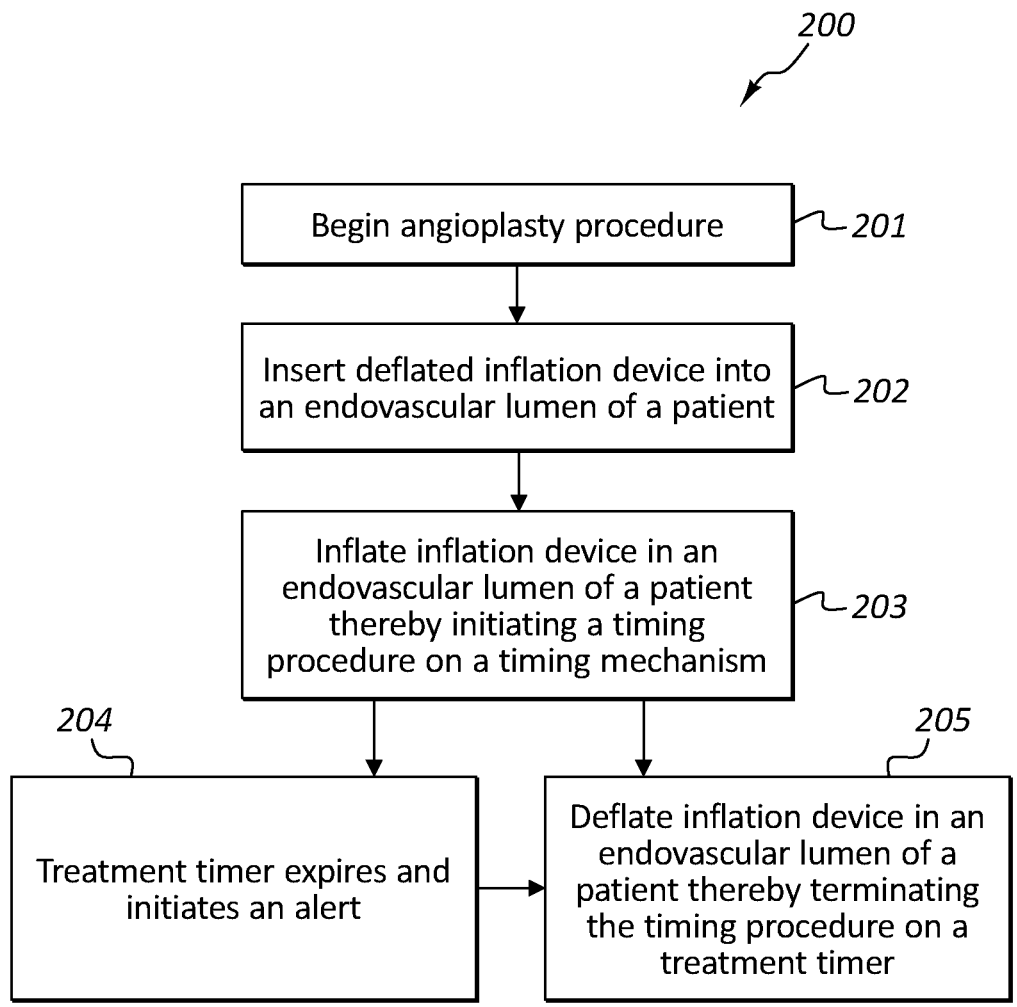
FIG. 2 is a flow chart of a method for timing the inflation time of an inflatable device as part of an angioplasty procedure.

FIG. 2 is a flow chart depicting an exemplary method 200 for performing an angioplasty procedure using a timing mechanism. The first step 201 of the illustrated method 200 is "Begin angioplasty procedure." Various procedures or steps for beginning an angioplasty procedure are within the scope of this disclosure and include, though may not always require: administering anesthetics to a patient, using a delivery device to insert a deflated inflation device into an endovascular lumen of a patient, and advancing the inflation device to a treatment site within the endovascular lumen.

In the illustrated embodiment, the second indicated step 202 of the method 200 is "Insert deflated inflation device into an endovascular lumen of a patient." As indicated above, during an angioplasty procedure, an inflation device may be inserted in a deflated state into a lumen of a patient using a delivery device to place the inflation device in the desired position in the lumen of the patient.

The third step 203 of the illustrated method 200 is indicated as "Inflate inflation device in an endovascular lumen of a patient thereby initiating a timing procedure on a treatment timer." In some angioplasty procedures, the inflation device is inflated within the endovascular lumen (also referred to as "vasculature lumen" and one example of a "body lumen") to unblock or otherwise treat the endovascular lumen. However, once the inflation device is inflated, it may itself tend to block or partially block the body lumen and prevent blood flow. Thus, during some procedures, a practitioner may desire to measure or limit the time intervals for which the inflation device is inflated to avoid trauma to the patient.

In some embodiments of the method 200, an inflation pump is used to inject fluid through a lumen in a tube and into the inflation device. The fluid may be a liquid or a gas. Further, in some embodiments of the method 200, the inflation pump is equipped with a pressure sensor to detect the pressure inside the lumen in the tube. The pressure sensor may be configured such that when it reads a pressure above a first threshold level, or a trigger pressure, a timing mechanism initiates measuring a treatment interval ("treatment timer"). This trigger pressure may be set as the pressure at which the inflation device is fully inflated, or it may be a pressure high enough to indicate it is likely the practitioner is inflating the device, though it is not fully inflated. In some embodiments of the method 200, the first threshold level or trigger pressure is approximately three pounds per square inch, approximately five pounds per square inch, or approximately eight pounds per square inch. Stated differently, the first threshold pressure may be 2-4 pounds per square inch, 3-5 pounds per square inch, 4-6 pounds per square inch, 5-7 pounds per square inch, 6-8 pounds per square inch, or 7-9 pounds per square inch.

After the third step 203 of the illustrated method 200, either step 204 or 205 occurs. If the treatment timer expires before the practitioner deflates the inflation device below the first threshold pressure, the method 200 proceeds to the fourth step 204. Step four 204 of the method 200 is "Treatment timer expires and initiates an alert." If the treatment timer expires by either completing a countdown to zero or a count up to a specified time, the timing mechanism initiates an alert. The treatment alert may be intended to notify a medical professional that the treatment timer has expired, for example, indicating that the inflation device has been inflated above the first threshold pressure for a certain time interval. The treatment alert may have one or more characteristics of the alerts described in connection with the method of FIG. 1.

The fifth step 205 of the method 200 is "Deflate inflation device in an endovascular lumen of a patient thereby terminating the timing procedure on a treatment timer." In instances wherein the practitioner deflates the inflation device before the treatment timer elapses, the method progresses from step 203 to 205, rather than from step 203 to 204. This deflation may be indicated by the pressure sensor reading a pressure below a second threshold level, which may or may not be the same value as the first threshold value discussed above. Thus, in some embodiments of the method 200, when the pressure sensor senses a pressure below a second threshold level, the treatment timer stops and the countdown or count up procedure may temporarily pause until the pressure sensor again senses a pressure above the first threshold level. In other embodiments, when the pressure sensor senses a pressure below a threshold level, the treatment timer resets to the same state it was in before the pressure sensor sensed a pressure above the first threshold level. The first threshold level may be greater than the second threshold level, the same as the second threshold level, or less than the second threshold level.

Other embodiments of a method for performing an angioplasty procedure using a timing mechanism comprise one or more of the steps of method 200 described herein. In some of these embodiments, the steps of the method 200 may be performed in an order different from that described in method 200.

FIGS. 3-8 depict representations of several embodiments of method 100 as described above. It should be noted that the procedures depicted in FIGS. 3-8 are specific examples of the more general method 100 as described, and thus do not limit the scope of the method 100 above.

Figure 3:
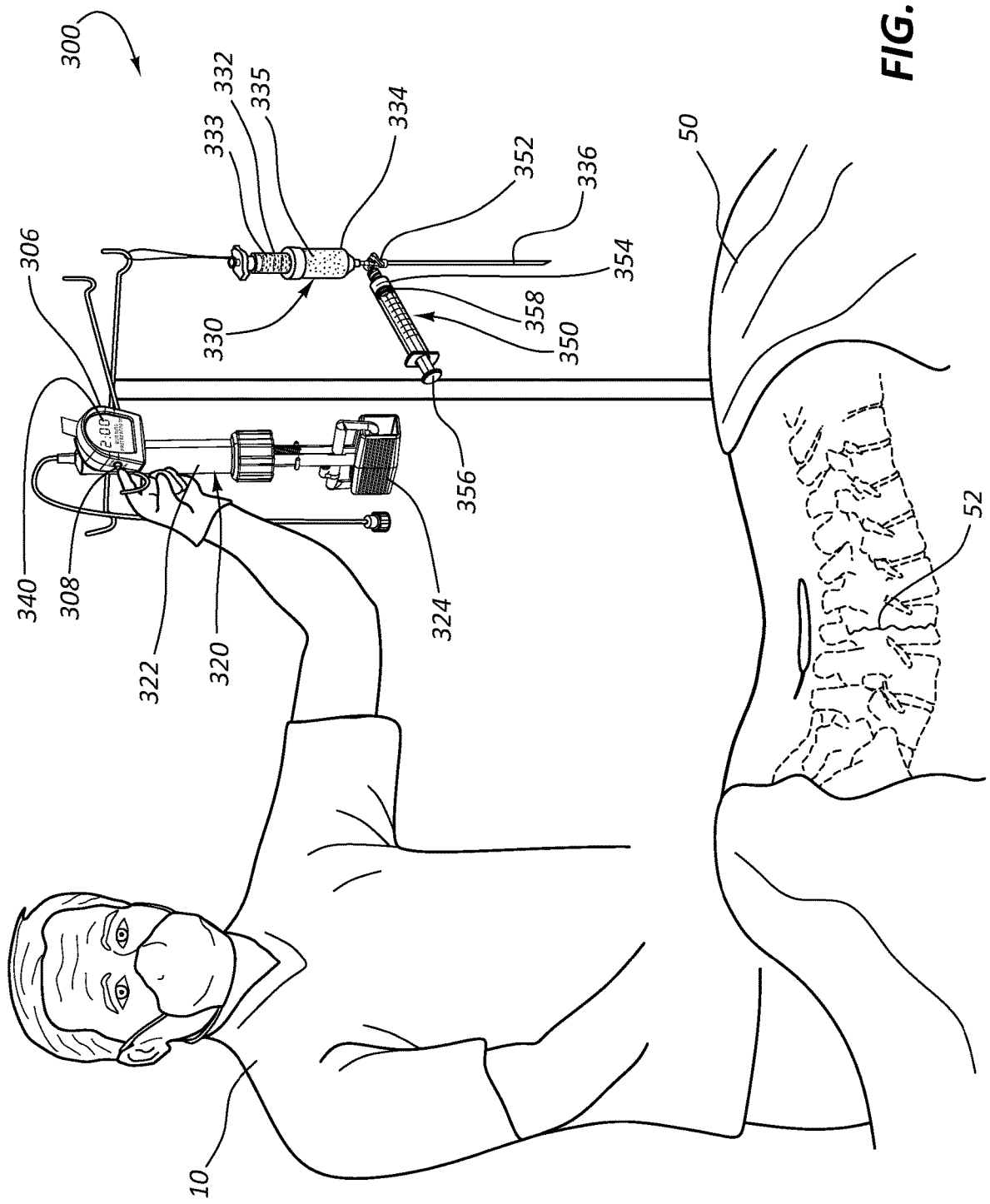
FIG. 3 is a medical practitioner starting a pre-treatment timer.

FIG. 3 is a depiction of a medical practitioner 10 initiating a pre-treatment timer on a timing mechanism 306. In FIG. 3, the medical practitioner 10 is initiating a pretreatment timer by pushing a start button 308. The timing mechanism 306 has a display 340 indicating the remaining time for the pretreatment procedure. In some embodiments of the timing mechanism 306, the timing mechanism has a sensor for detecting pressure in a chamber 322, and the display 340 comprises a pressure reading from the sensor. The timing mechanism 306 is coupled to an injector 320 (e.g., an injection pump).

The injector 320 comprises the chamber 322 and a handle 324. The chamber 322 houses a fluid material. In some embodiments of the injector 320, the fluid material housed in the chamber 322 is a gas. In other embodiments of the injector 320, the fluid material housed in the chamber 322 is an incompressible fluid such as water or saline. The handle 324 is coupled to a plunger that is configured to be advanced through the chamber 322 to dispense the fluid material.

FIG. 3 also shows a cannula 336 for injecting material into a vertebra 52 of a patient 50. The cannula 336 is attached to a dispensing device 330 (which may also function as a storage container) comprising a second chamber 334 housing a second ingredient 335, an upper chamber 332 housing a first ingredient 333 and a syringe 350 comprising a plunger 356 with a seal 358 and a chamber 354 connected to the lower portion of the lower chamber 334 through a valved connector 352. In some embodiments, the second ingredient 335 is a set of dry ingredients. In some embodiments, the first ingredient 333 is a set of fluid ingredients.

Figure 4:
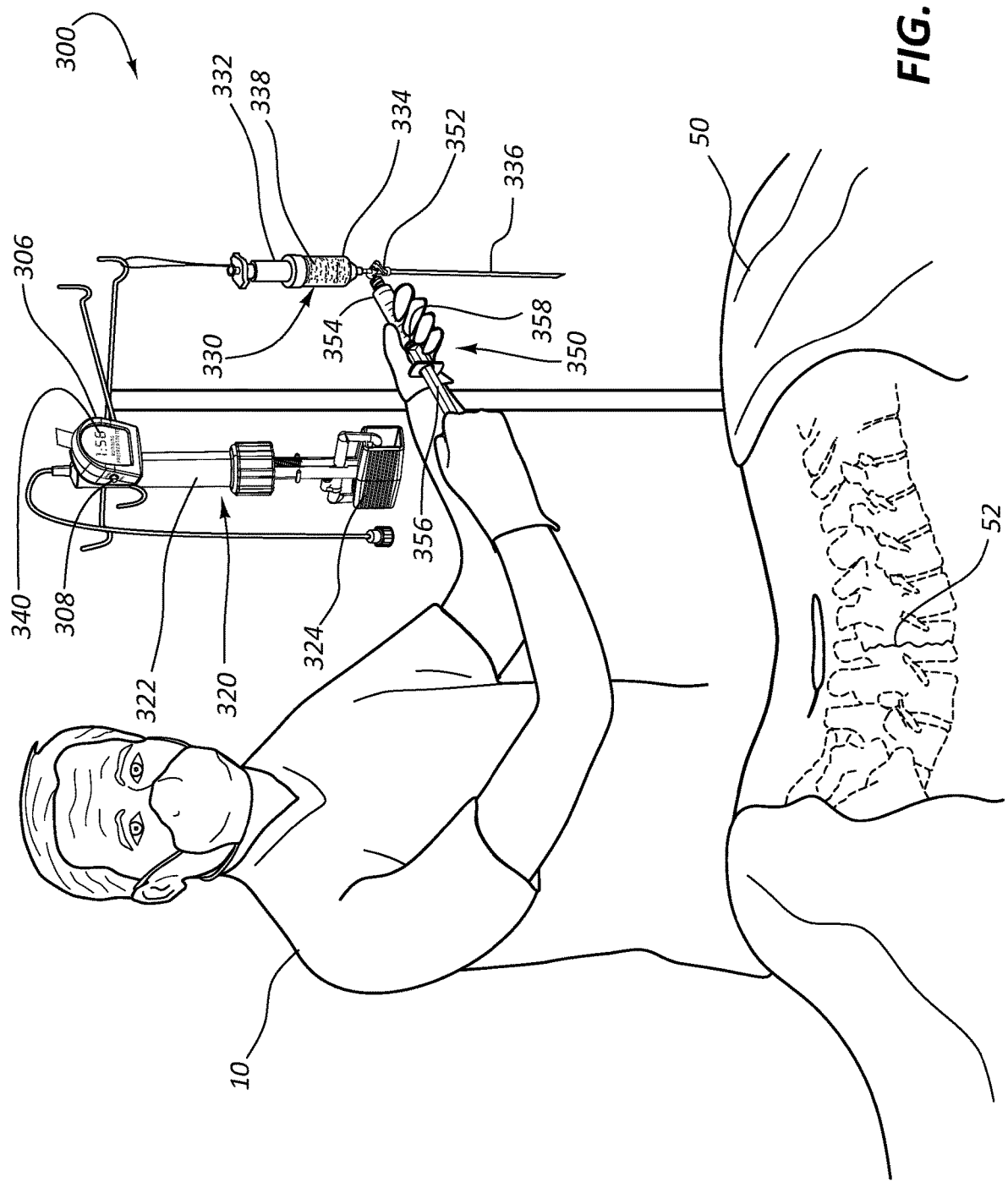
FIG. 4 is a medical practitioner performing a pre-treatment procedure.

FIG. 4 depicts the medical practitioner 10 performing a pre-treatment procedure by retracting the plunger 356 of the syringe 350. Retraction of the plunger 356 causes a vacuum in the chamber 354. The vacuum in the chamber 354 causes the first ingredient 333 to enter the second chamber 334 and combine with the second ingredient 335 to create a mixture 338. Also shown in FIG. 4 is a countdown of a timer in progress on the display 340 of the timing mechanism 306. The pre-treatment timer is counting down the amount of time for the mixture to be ready for injection into the vertebra 52 of the patient 50.

Figure 5:
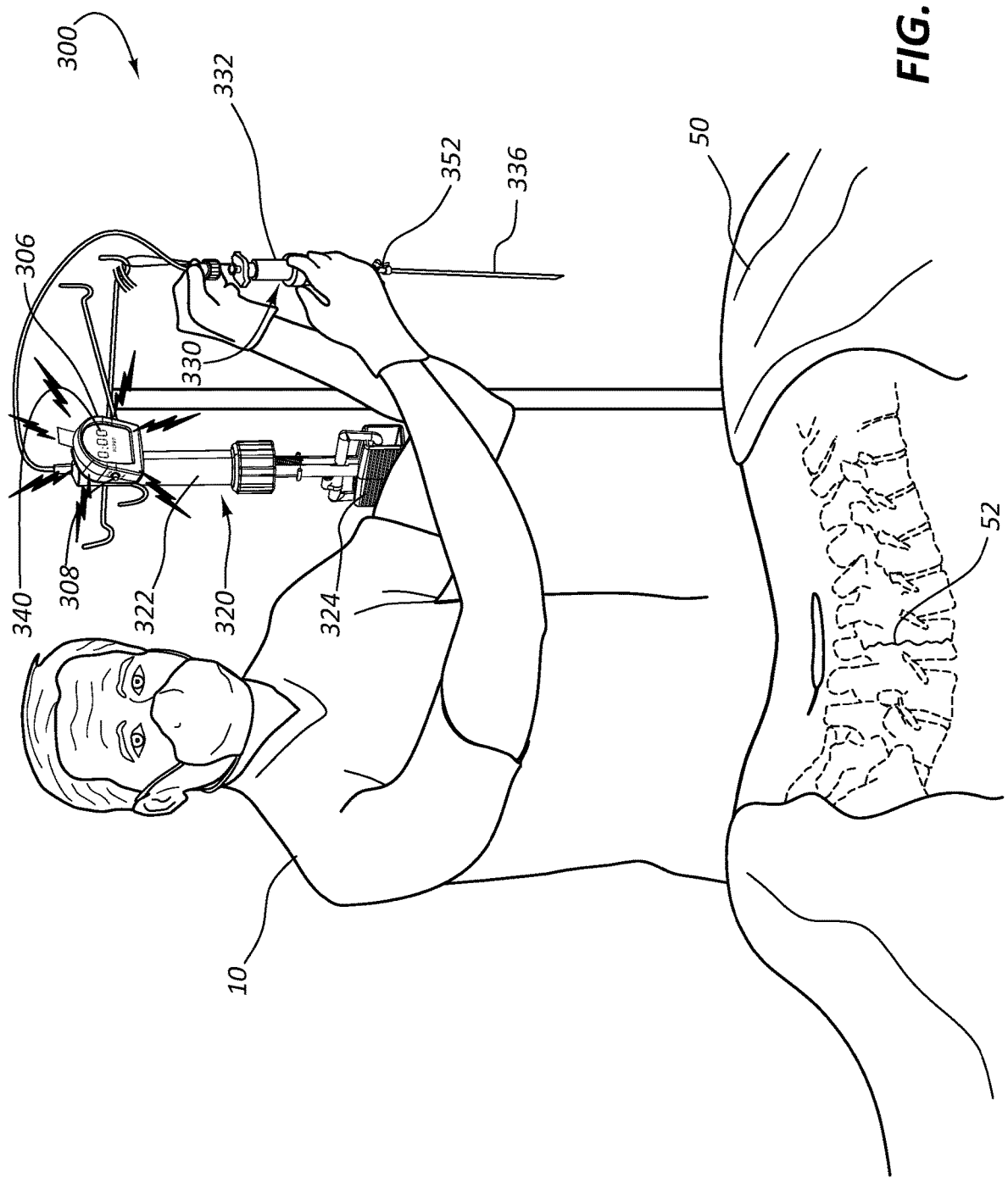
FIG. 5 is an alarm indicating termination of the pre-treatment timer.

FIG. 5 depicts a termination of the pre-treatment timer with the display 340 of the timing mechanism 306 showing "0:00" and an alarm having been initiated on the timing mechanism 306. The alarm is indicating that the mixture 338 is ready for use by the medical practitioner 10 for a procedure. Also shown in FIG. 5 is the medical practitioner 10 connecting the injector 320 to the dispensing device 330 via tubing.

Figure 6:
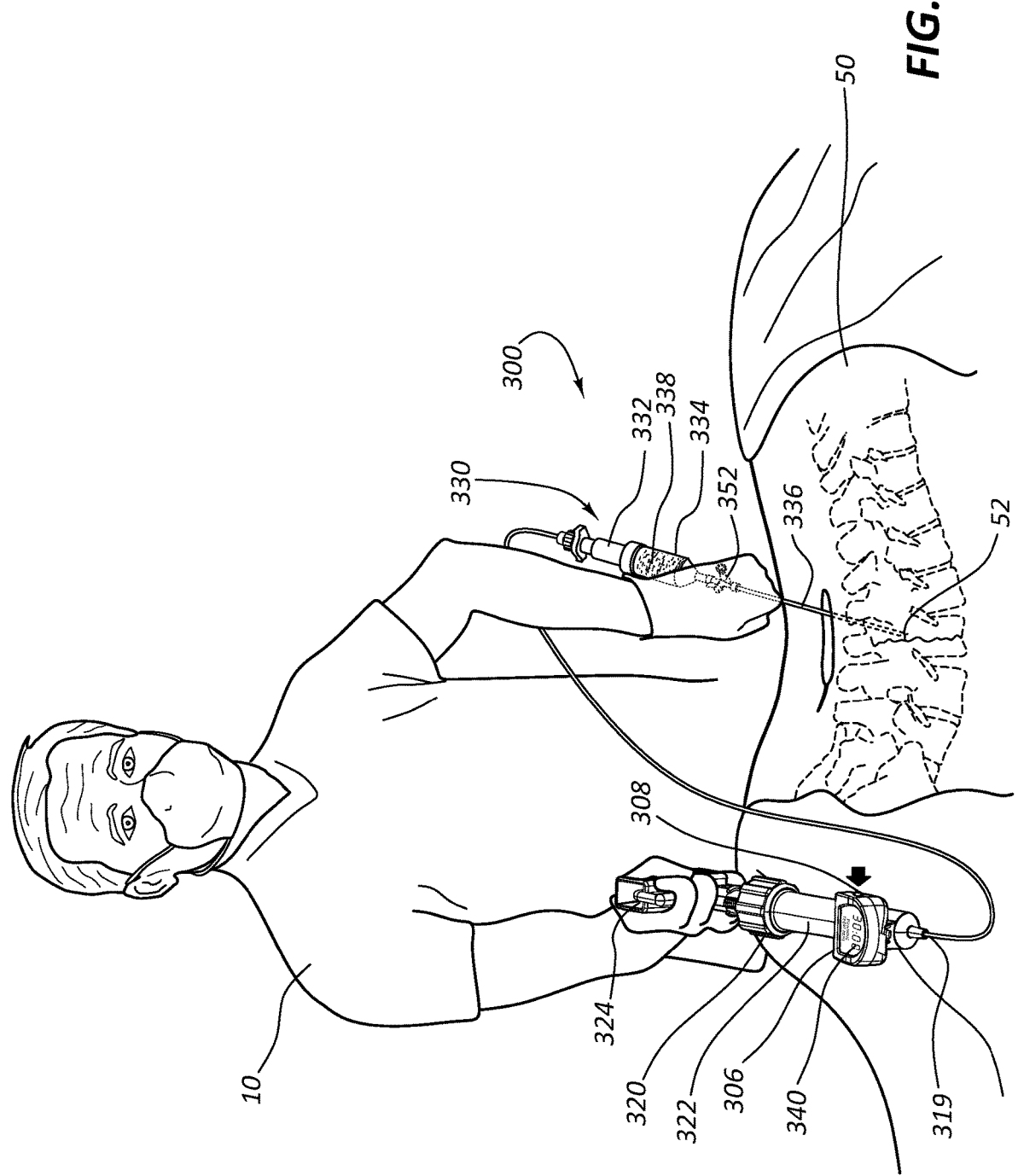
FIG. 6 is a medical practitioner performing a treatment procedure.

In FIG. 6, the medical practitioner 10 is performing a treatment procedure by inserting a delivery end of the cannula 336 into the vertebra 52 of the patient 50 and injecting the mixture 338 through the cannula 336 using pressure from the injector 320. To expel the mixture 338 from the dispensing device 330, the medical practitioner 10 advances the plunger of the injector 320 through the chamber 322 causing the fluid inside to progress through the connecting tubing to the upper chamber 332 to advance a plunger within the upper chamber 332 through the second chamber 334. In some embodiments of the injector 320, the medical practitioner 10 views the display 340 to see the pressure exerted on the fluid (and by translation, the plunger in the lower chamber) thereby allowing the medical practitioner 10 to maintain a controlled flow of the mixture 338 into the vertebra 52 of the patient 50.

Also shown in FIG. 6 is the display 340 showing a treatment timer for counting down the time allowed for the treatment procedure. This timer indicates the amount of time left before the mixture 338 is no longer fit for injection. This treatment timer may begin its countdown automatically upon expiration of the pre-treatment countdown or may be manually initiated.

Figure 7:
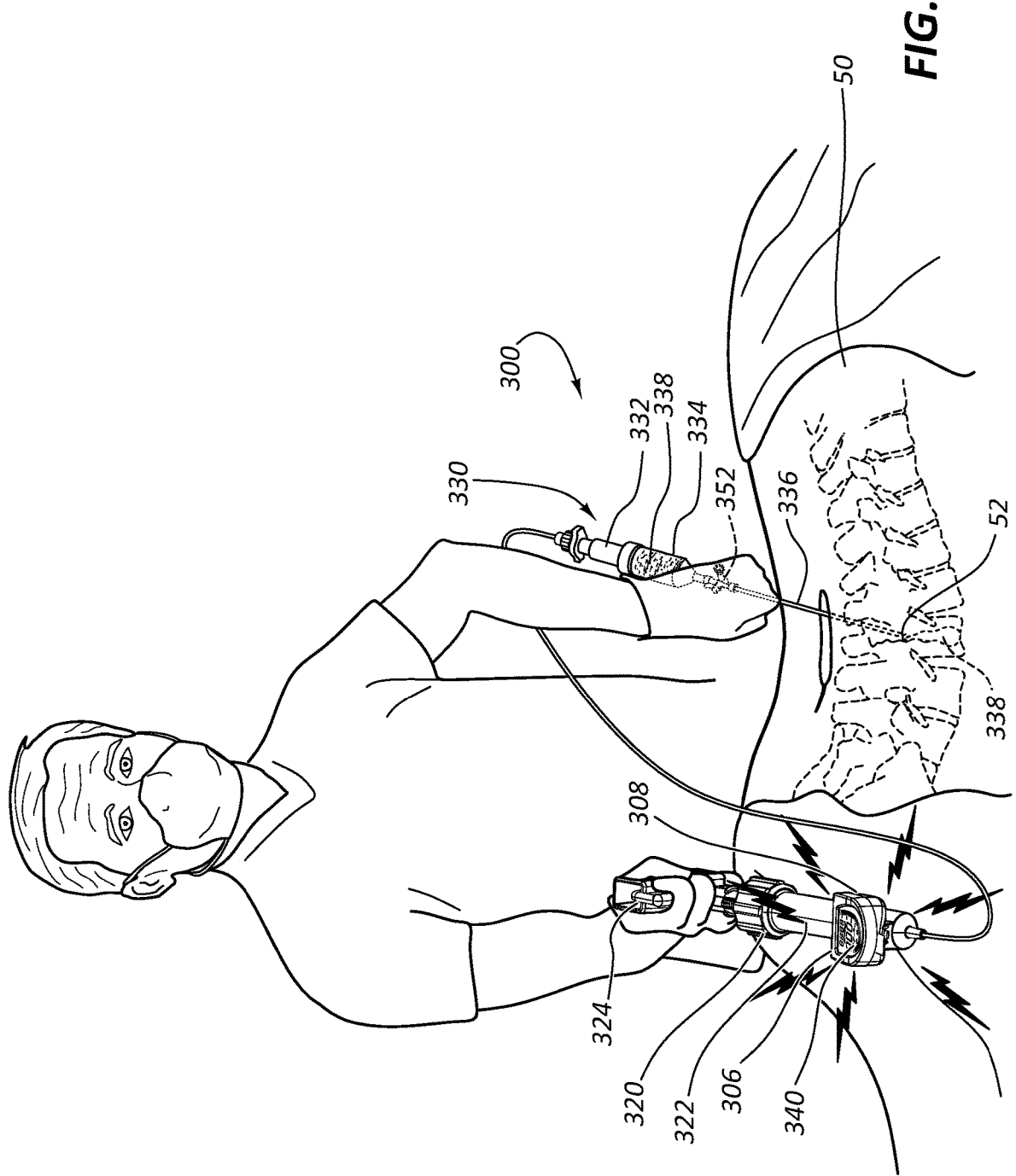
FIG. 7 is an alarm indicating termination of the treatment timer.

FIG. 7 shows the display 340 showing "0:00" indicating that the mixture 338 is no longer indicated for injection and therefore the procedure should terminate. The timing mechanism 306 initiates an alarm to indicate to the medical practitioner 10 that the procedure should terminate. Also shown in FIG. 7 is the mixture 338 in the vertebra 52 of the patient 50.

In some instances the alarm at the conclusion of the treatment timer may be identical to that of the pre-treatment timer; in other examples they may differ. In some instances, the pre-treatment timer comprises a single audible tone while the treatment timer comprises a succession of multiple audible tones. Still further, upon expiration of the treatment timer, the display 340 may continue to flash "0:00" to indicate expiration of the treatment timer, or may begin to count up to track the amount of time elapsed since expiration of the treatment timer. In some embodiments the color of the text may change (for example to red) when tracking this over-time interval.

Figure 8:
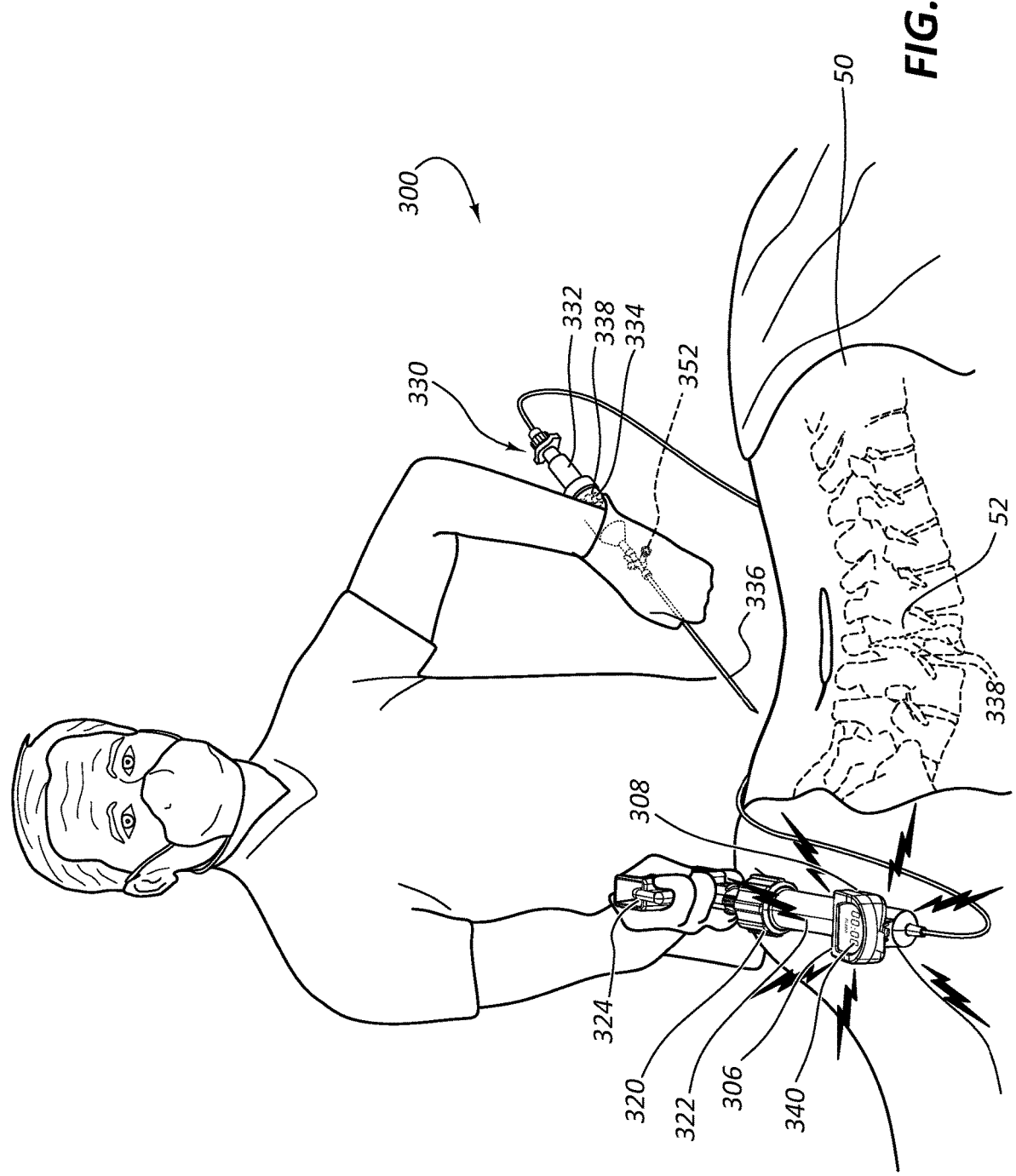
FIG. 8 is a medical practitioner terminating a treatment procedure in response to the alarm.

FIG. 8 shows the medical practitioner 10 terminating the procedure in response to the alarm on the timing mechanism 306.

Figure 9:
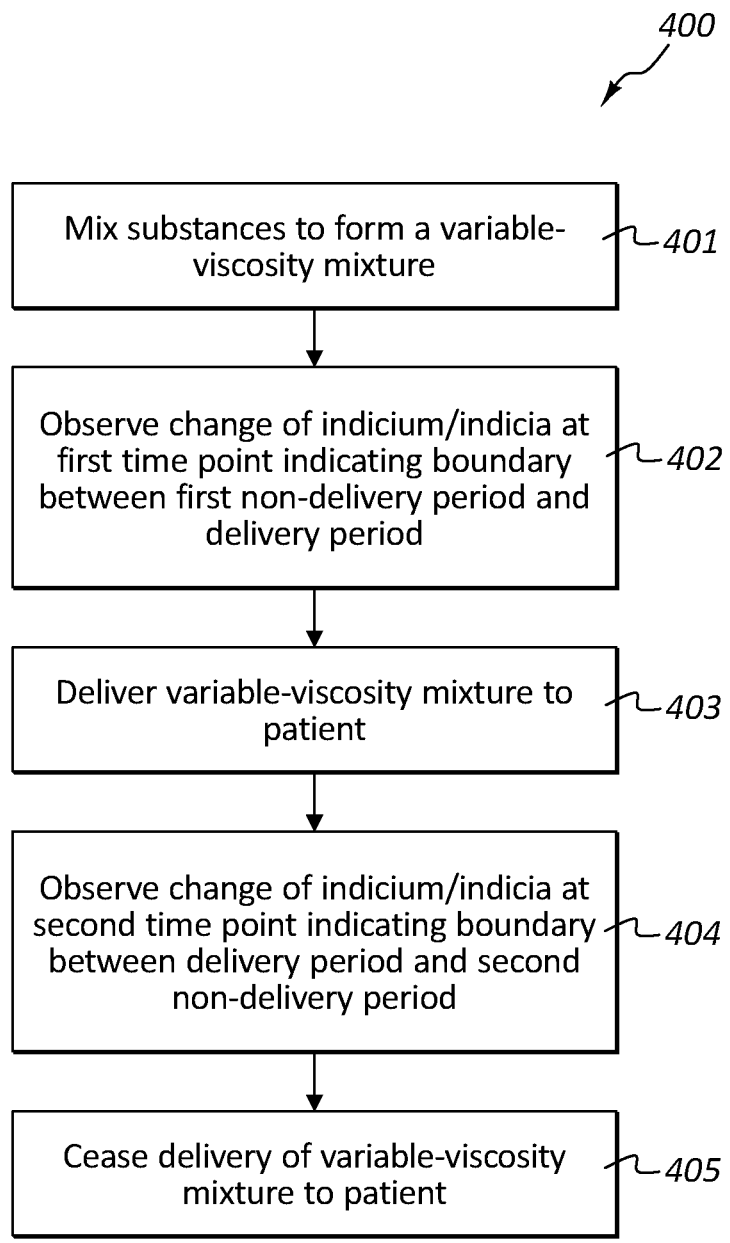
FIG. 9 is a flow chart of a method for delivering a mixture to a patient.

FIG. 9 is a flow chart of one embodiment of a method 400 for delivering a mixture to a patient. The method 400 may include the step 401 of mixing substances to form a variable-viscosity mixture. In some embodiments, the substances react with one another in an exothermic reaction. In some embodiments, the variable-viscosity mixture may initially be of insufficient viscosity for delivery to a patient. In other words, the viscosity may be too "runny," thereby preventing targeted delivery of the mixture to a particular region within the patient. Stated differently, the variable-viscosity mixture may initially be unsuitable for localized delivery. In other embodiments, the variable-viscosity mixture is of suitable viscosity immediately after mixing of the substances that form the mixture.

In embodiments, where the variable-viscosity mixture is initially of insufficient viscosity, the variable-viscosity mixture may, over time, increase in viscosity. As the variable-viscosity mixture increases in viscosity, the practitioner may observe 402 a change of one or more indicia at a first time point. The change of the one or more indicia at the first time point may demarcate a boundary between a first non-delivery period and a delivery period. In other words, prior to the change of the one or more indicia at the first time point, the practitioner should not attempt to deliver the variable-viscosity mixture to the patient, as the variable-viscosity mixture may have a viscosity that is too low. However, once the one of more indicia change at the first time point, the practitioner understands that the variable-viscosity mixture is of suitable viscosity for delivery to a patient.

Accordingly, during this delivery period, the practitioner may deliver 403 the variable-viscosity mixture to the patient. For example, in some embodiments, a variable-viscosity cement is introduced into one or more vertebra of a patient. In other embodiments, the variable-viscosity mixture is delivered to some other location within the patient, such as into one or more teeth to fill one or more cavities.

As the variable-viscosity mixture continues to increase in viscosity, the practitioner may observe 404 another change in the one or more indicia at a second time point. The change of the one or more indicia at the second time point may demarcate a boundary between the delivery period and a second non-delivery period. In other words, once the one or more indicia change at the second time point, the practitioner should cease 405 delivering the variable-viscosity mixture to the patient, as the mixture is (or will soon become) too viscous for its intended use.

One or both of the first time point and the second time point may be determined, at least in part, by input from a sensor. In other words, when the first time point and/or the second time point occur may be a function of input from the sensor.

In some embodiments, the sensor is a temperature sensor. In some embodiments, the temperature sensor is configured to sense ambient temperature. In other or further embodiments, the temperature sensor is configured to sense the temperature of the variable-viscosity mixture. In some instances, the temperature sensor may sense the temperature of the variable-viscosity mixture while the mixture is disposed within a delivery device. In some instances, the temperature sensor may sense the temperature of the mixture as the variable-viscosity mixture is ejected from the delivery device. In some instances, a plurality of temperature sensors are used.

In other or further embodiments, the one or more sensors comprise a pressure sensor. The pressure sensor(s) may be configured to detect the pressure within a chamber of the delivery device. For example, one or more pressure sensors may be used to determine the pressure within one or both of (1) a chamber that encompasses the variable-viscosity mixture and (2) a chamber that houses fluid (e.g., water or saline) used to displace the variable-viscosity mixture. Input from the pressure sensor(s) may be used to, at least in part, determine the first time point and/or the second time point. Additionally or alternatively, in some embodiments, the one or more sensors include a sensor that detects the amount of mixture remaining within the delivery device. Input from such sensors may be used to determine, at least in part, the first time point and/or the second time point. Stated differently, in some embodiments, a delivery period is determined by detecting the volume of mixture that has been administered to the patient.

By using information provided by one or more of the sensors, a system may be configured such that the one or more indicia provide more accurate information regarding the viscosity of the variable-viscosity mixture than some systems which fail to obtain or use such information. For example, by determining the temperature of a variable-viscosity mixture and/or the ambient environment, the system may better assess when a temperature-dependent variable-viscosity mixture is (or will become) too viscous for use. The inputs from the sensors may be received in a dynamic fashion. In other words, data from the sensors may be obtained over various time points. The dynamic input may be used to more accurately determine and/or estimate the viscosity (or range of change in viscosity) for the variable-viscosity mixture. For example, in an embodiment that uses one or more count-down timers to estimate when a first time point and/or a second time point are to occur, the remaining time on the count-down timer may change in a non-linear fashion to account for new data from the sensors. In other words, the time readout (e.g., the time until the next time point) may be a function of one or more measured input parameters).

FIGS. 10-15 depict a system 500 for delivering a mixture to the patient. The embodiment depicted in FIGS. 10-15 resembles the system 300 described above in certain respects. Accordingly, like features are designated with like reference numerals, with the leading digits incremented to "5." For example, the embodiment depicted in FIGS. 10-15 includes an injector 520 that may, in some respects, resemble the delivery injector 320 of FIGS. 3-8. Relevant disclosure set forth above regarding similarly identified features thus may not be repeated hereafter. Moreover, specific features of the system 300 and related components shown in FIGS. 3-8 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the system 500 and related components depicted in FIGS. 10-15. Any suitable combination of the features, and variations of the same, described with respect to the system 300 and related components illustrated in FIGS. 3-8 can be employed with the system 500 and related components of FIGS. 10-15, and vice versa.

As noted above, FIGS. 10-15 provide various perspective views of a system 500 for delivering a mixture to patient 50. Each of FIGS. 10-15 show the system 500 in different states of a medical procedure.

As shown in FIGS. 10-15, the system 500 may include an injector 520 and a storage container 530, which together constitute a delivery device 510. The injector 520 may include a fluid chamber 522, a handle 524, a plunger 526, and a distal connector 528. The handle 524 may be attached to the plunger 526 such that advancement of the handle 524 in a distal direction causes the plunger 526 to move in a distal direction, thereby pushing fluid within the fluid chamber 522 toward the distal end of the injector 520. In some embodiments, fluid within the fluid chamber 522 is a compressible gas. In other embodiments, the fluid within the fluid chamber 522 is an incompressible fluid, such as water or saline.

The storage container 530 may include a first chamber 532 and a second chamber 534. The first chamber 532 may initially house a first substance 533, while the second chamber 534 initially houses a second substance 535 that differs from the first substance 533. For example, the first chamber 532 may initially house a liquid (e.g., water, saline, ethanol), while the second chamber 534 houses one or more dry substances or a paste. The storage container 530 may be coupled to a cannula 536.

Figure 10:
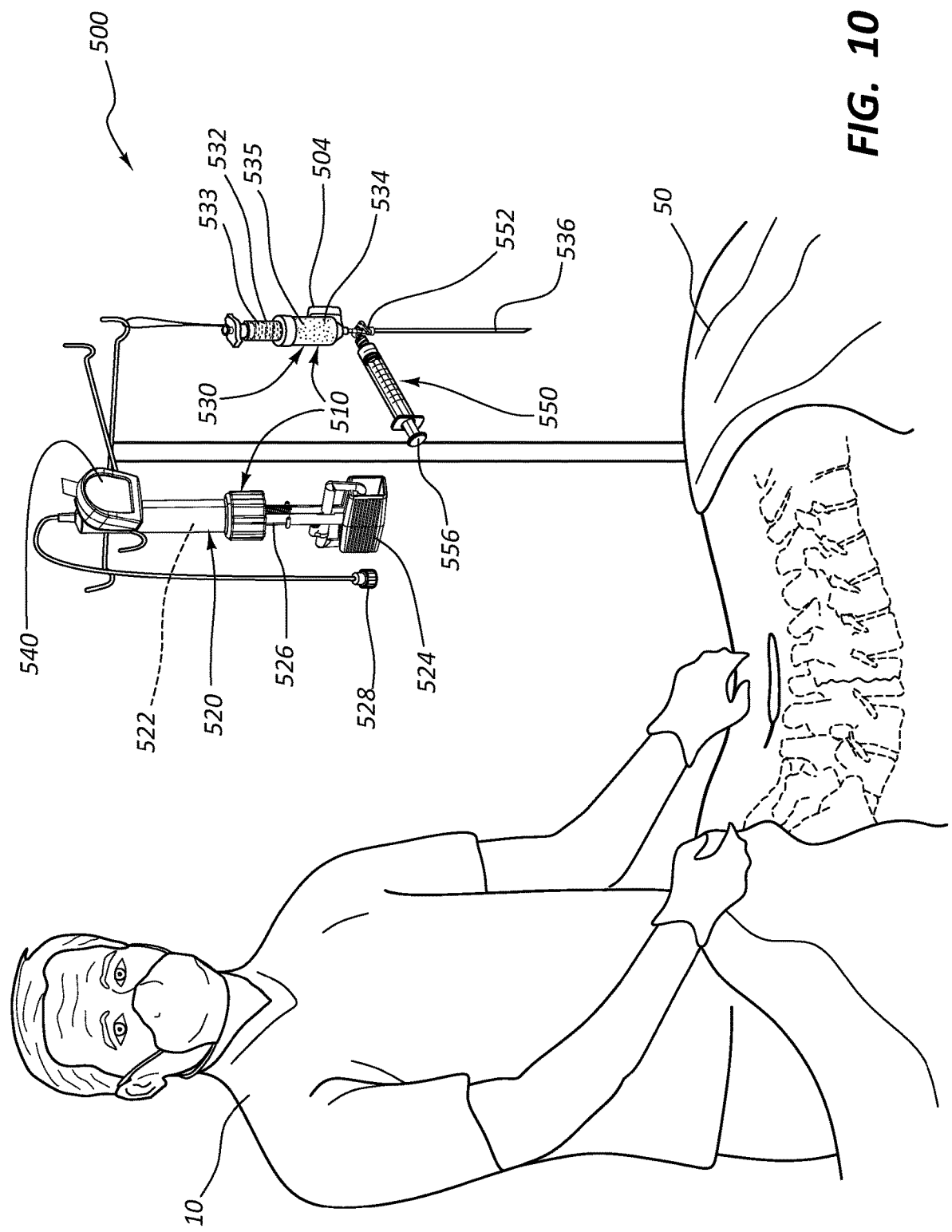
FIG. 10 is a perspective view of a system for delivering a mixture to a patient, with the system in a first state.
Figure 11:
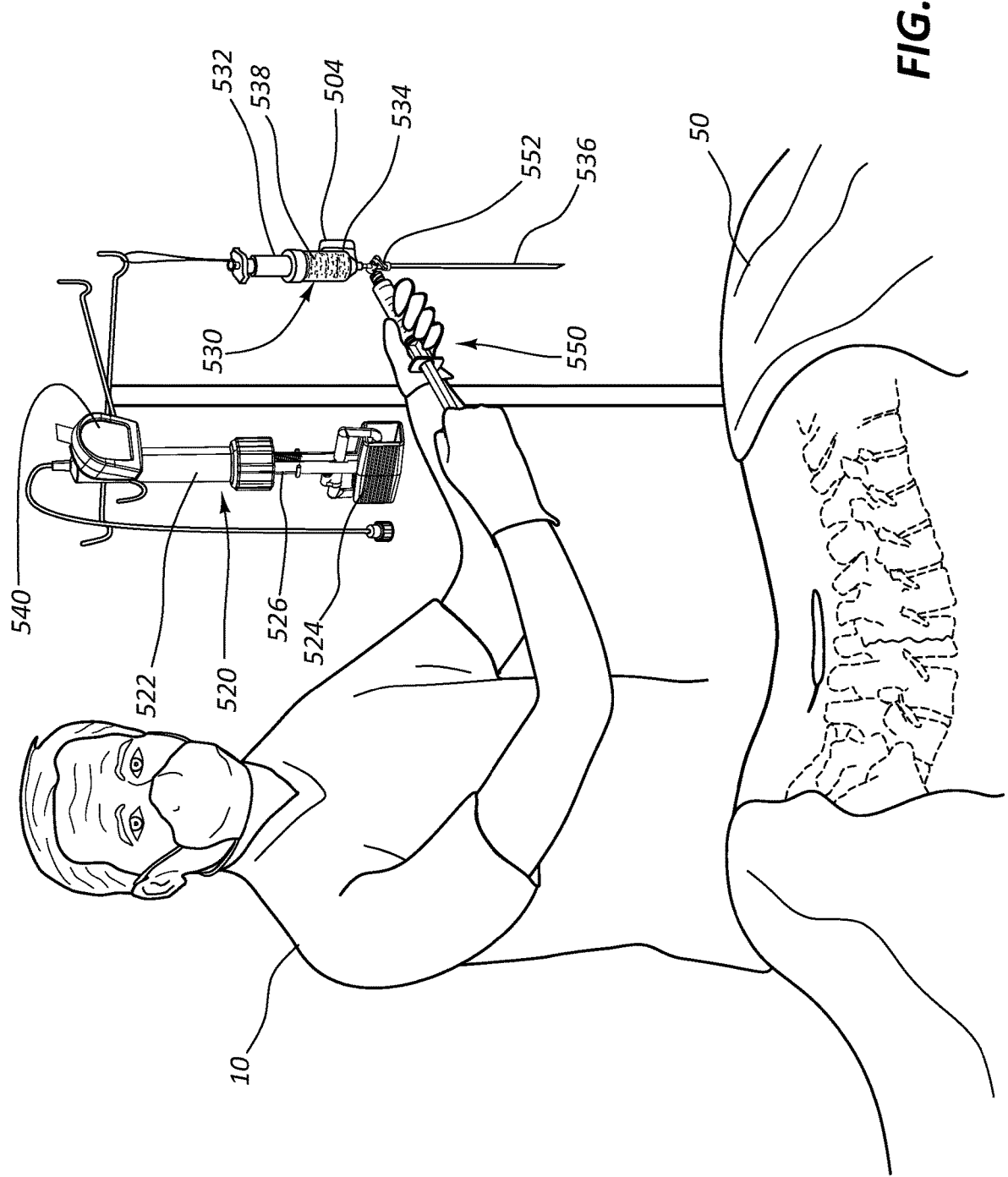
FIG. 11 is a perspective view of the system of FIG. 10 in a second state.

As shown in FIGS. 10 and 11, the first substance 533 in the first chamber 532 may be mixed with the second substance 535 in the second chamber 534 to create a variable-viscosity mixture 538. For example, in some embodiments, a plunger of a syringe 550 that is coupled to the second chamber 534 via a valved connector 552 may be retracted, causing a reduction in pressure within the chamber of the syringe 550. The reduction of pressure may cause the first substance 533 to enter into the second chamber 534 and mix with the second substance 535.

In some embodiments, the resulting variable-viscosity mixture 538 changes viscosity at a relatively rapid rate. For example, in some embodiment, the variable-viscosity mixture 538 becomes substantially solid within 8 hours, 5 hours, 2 hours, 1 hour, 30 minutes, 15 minutes, 10 minutes, and/or 5 minutes at standard ambient temperature and pressure. In some embodiments, the variable-viscosity mixture 538 is suitable for delivery into the patient 50 for less than 10 minutes, less than 5 minutes, less than 4 minutes, less than 3 minutes, less than 2 minutes, and/or less than 1.5 minutes at standard ambient temperature and pressure. Stated differently, in some embodiments, the delivery period is less than 10 minutes, less than 5 minutes, less than 4 minutes, less than 3 minutes, less than 2 minutes, and/or less than 1.5 minutes at standard ambient temperature and pressure.

Once the first substance 533 is mixed with the second substance 535 to form the variable-viscosity mixture 538, the system 500 may provide information to the practitioner 10 to help the practitioner 10 determine when the variable-viscosity mixture 538 is and/or will be of suitable viscosity for injection into the patient 50. Stated differently, the system 500 may include one or more indicia that are configured to automatically transition between states, thereby indicating boundaries between non-delivery period(s) and a delivery period. In some embodiments, the one or more indicia include one or more visible indicia. In other or further embodiments, the one or more indicia include one or more audible indicia. In some embodiments, the one or more indicia include haptic (e.g., tactile) indicia.

Figure 12:
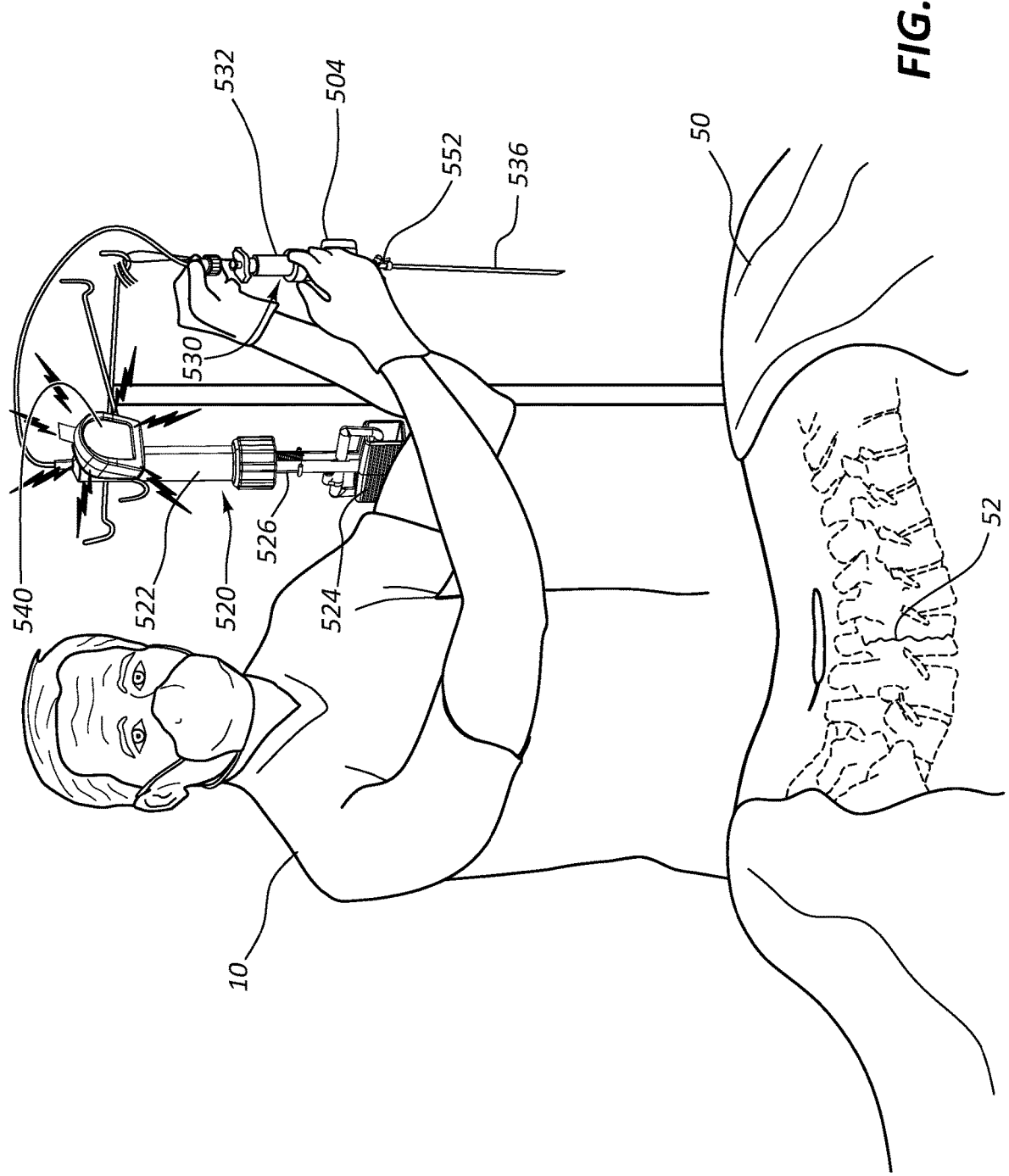
FIG. 12 is a perspective view of the system of FIGS. 10-11 in a third state.

For example, in some embodiments, the system 500 includes a display 540 (e.g., a display screen) for displaying information that helps the practitioner 10 determine when the variable-viscosity mixture is of suitable viscosity for delivery to the patient 50. The display 540 may display numeric and/or non-numeric indicia. In some embodiments, the display 540 displays a timer. In some embodiments, the timer indicates (e.g., counts down to) a time point in which the variable-viscosity mixture 538 is of suitable viscosity for delivery to the patient 50. For example, when the count-down timer reaches zero at a first time point as shown in FIG. 12, the system may produce an audible sound that alerts the practitioner 10 that the variable-viscosity mixture 538 is of suitable viscosity for delivery to the patient 50. Also shown in FIG. 12 is a practitioner 10 connecting the injector 520 to the storage container 530.

The transition between states for one or both of visual indicia (e.g., the timer reaching 0:00") and audible indicia (e.g., the audible alarm) at the first time point, as depicted in FIG. 12, may indicate a boundary between a first non-delivery period and a delivery period. In other words, prior to the change of the one or more indicia at the first time point, the practitioner 10 should not attempt to deliver the variable-viscosity mixture 538 to the patient 50. However, once the one of more indicia change at the first time point, the practitioner 10 understands that the variable-viscosity mixture 538 is of suitable viscosity for delivery to the patient 50.

Figure 13:
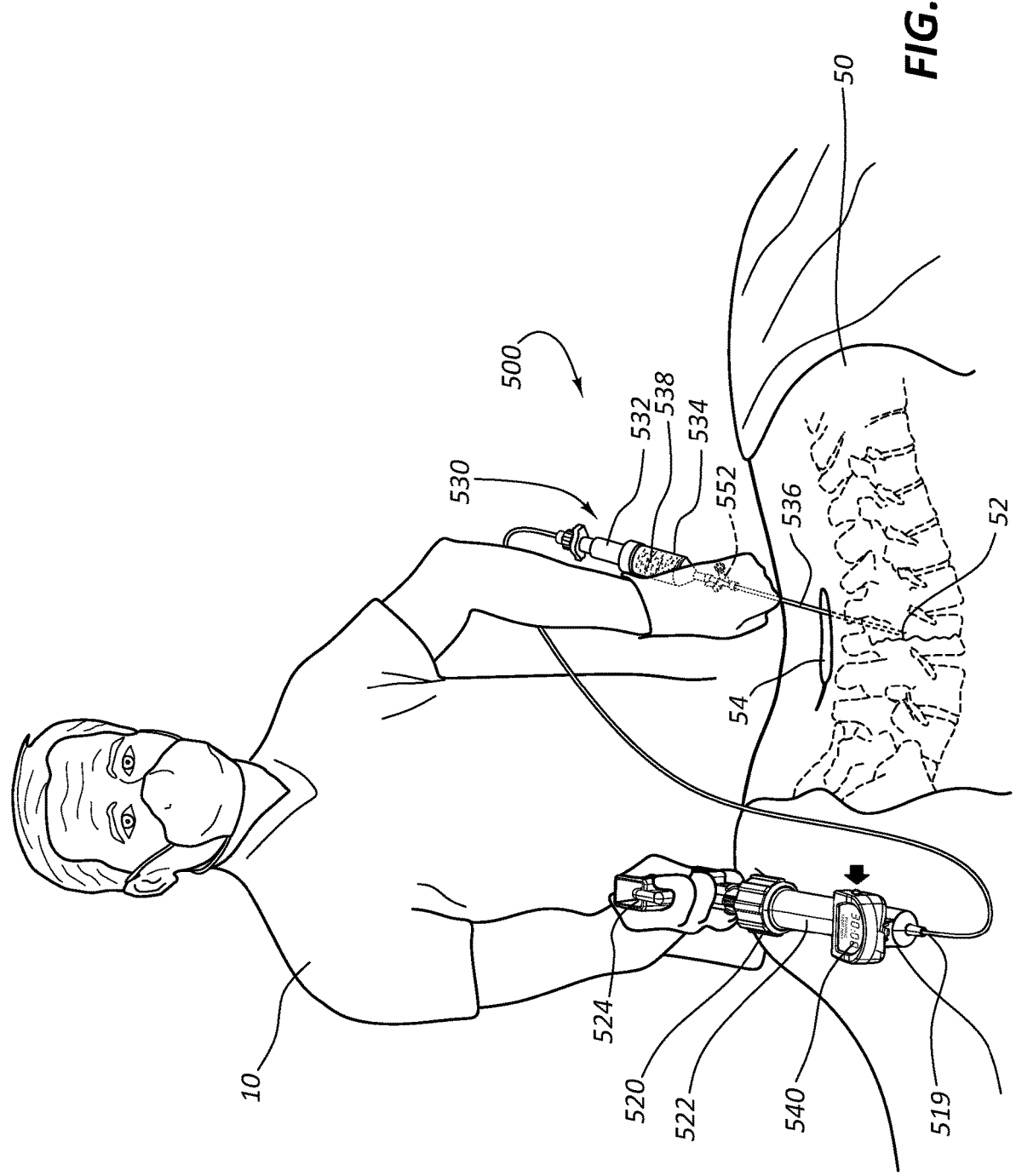
FIG. 13 is a perspective view of the system of FIGS. 10-12 in a fourth state.
Figure 14:
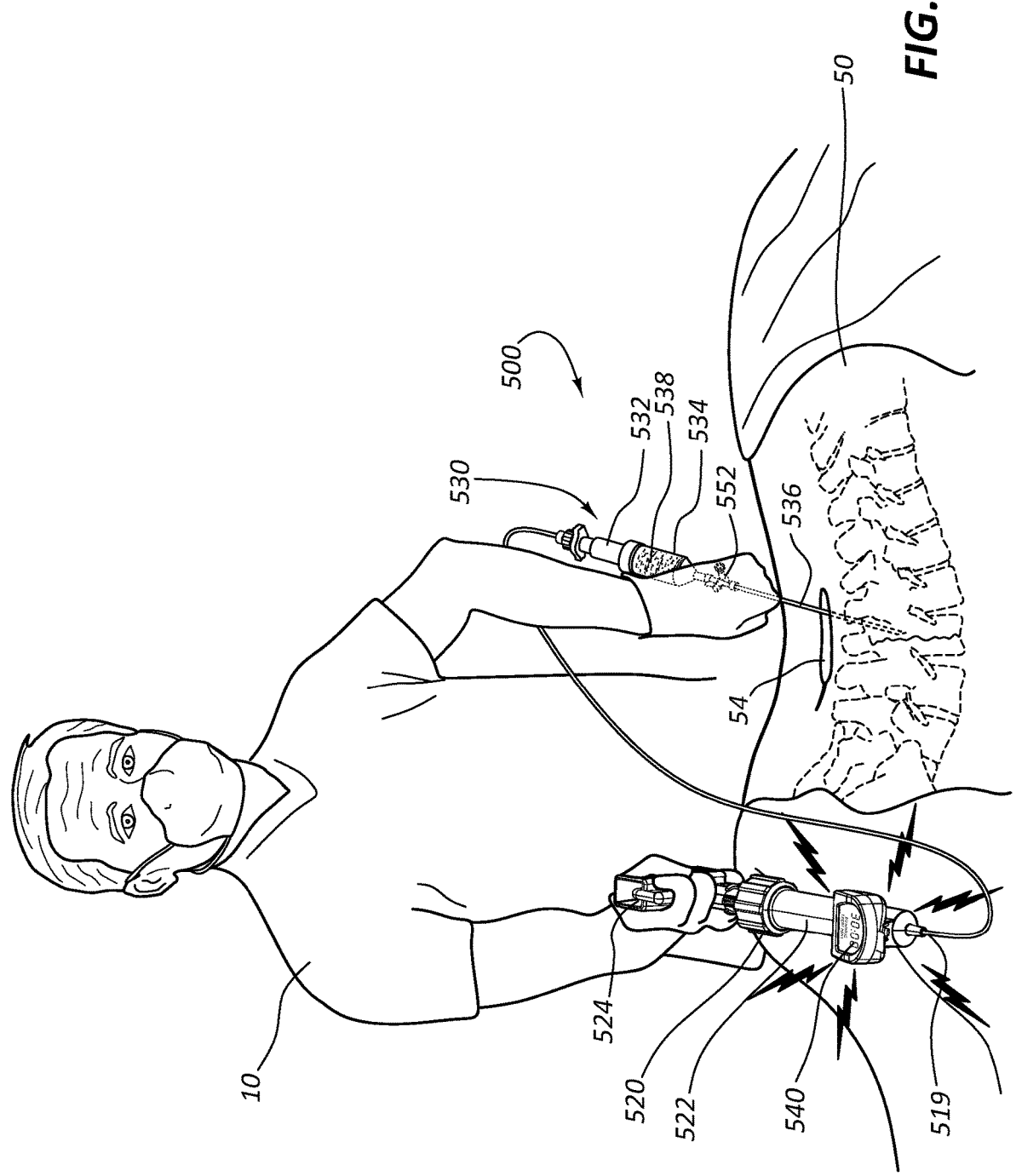
FIG. 14 is a perspective view of the system of FIGS. 10-13 in a fifth state.

Thus, in the period immediately following the first time point, the practitioner 10 may deliver the variable-viscosity mixture 538 from the delivery device 510 to the patient 50 as depicted in FIG. 13. For example, the distal end of the cannula 536 may be inserted through an incision 54 in the back of the patient 50 such that the distal tip of the cannula 536 is disposed within or adjacent to a vertebra of the patient 50. The variable-viscosity mixture 538 is then expelled from the delivery device 510 as the practitioner 10 advances the handle 524 of the injector 520 such that the plunger 526 moves in a distal direction, thereby pushing fluid within the fluid chamber 522 toward the storage container 530, which in turn pushes the variable-viscosity mixture 538 into a region (e.g., cavity) of the vertebra of the patient 50.

Figure 15:
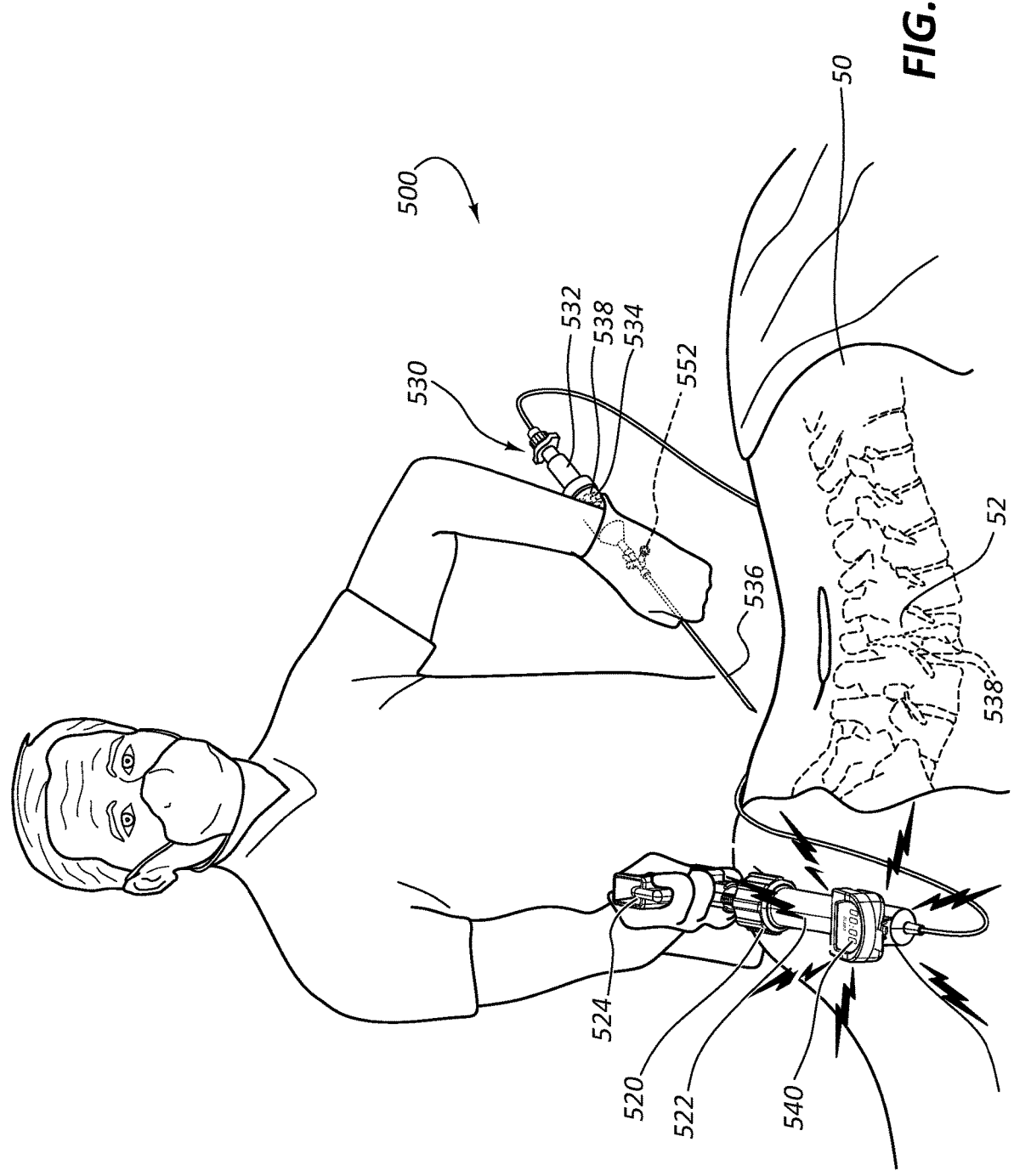
FIG. 15 is a perspective view of the system of FIGS. 10-14 in a sixth state.

Once the variable-viscosity mixture 538 becomes (or approaches becoming) too viscous for use, the one or more indicia of the system 500 may transition to a third state at a second time point as shown in FIG. 15. The second time point may indicate a boundary between the delivery period and a second non-delivery period. In other words, the practitioner 10 may deliver the variable-viscosity mixture 538 within a period of time between the first time point and the second time point, and cease delivering the variable-viscosity mixture 538 to the patient 50 as shown in FIG. 15 once the one or more indicia transition between states at the second time point.

The system 500, as shown and described in FIGS. 10-15, may also include one or more sensors. In some embodiments, the one or more sensors include one or more temperature sensors. Examples of suitable temperature sensors include thermisters, thermocouples, etc. Additionally or alternatively, the one or more sensors may include one or more pressure sensors. In some embodiments, the one or more sensors include a sensor for detecting the amount of variable-viscosity mixture 538 that remains within the delivery device 510.

In the embodiment depicted in FIGS. 10-15, they system 500 includes a housing 504 for one or more sensors. More specifically, in the depicted embodiment, the one or more sensors and the housing 504 are positioned on the storage container 530 such that at least one of the one or more sensors is in communication with the variable-viscosity mixture 538. In other or further embodiments, one or more sensors may be disposed at some other location. For example, in some embodiments, one or more sensors may be attached to the injector 520. In some embodiments, the one of more sensors are not coupled to the delivery device 510, but are instead disposed elsewhere in the room where the medical procedure is taking place.

In some embodiments where the one or more sensors include a temperature sensor, the temperature sensor may sense a temperature of the variable-viscosity mixture 538 when the variable-viscosity mixture 538 is disposed within the storage container 530 of the delivery device 510. In some embodiments, the temperature sensor senses a temperature of the ambient environment rather than (or in addition to) the temperature of the variable-viscosity mixture 538. Input from one or more temperature sensors may be used, at least in part, to determine the first and/or the second time point. In other words, when the first time point and/or the second time point occurs may be a function of the input provided by one or more temperature sensors.

More specifically, in some embodiments, the system 500 includes a processor and a data storage device (e.g., a non-transitory computer-readable medium) with instructions stored therein for calculating when a variable-viscosity mixture is of suitable viscosity for delivery to the patient 50 based on information (e.g., temperature information) from the one or more sensors. For example, response curves that calculate viscosity based on elapsed time at a given temperature may be programmed onto the data storage device. When executed by the processor, the instructions on the data storage device may perform operations that allow for the calculation of viscosity based on the elapsed time, the temperature of the environment and/or the variable-viscosity mixture 538, and/or a knowledge of the type of variable-viscosity mixture 538 that is being used.

The calculated viscosity may be relayed to a display 540 or other output, thereby allowing a practitioner 10 to observe the viscosity of the variable-viscosity mixture 538 over the course of the medical procedure. Stated differently, in some embodiments, the display 540 displays the real-time (or semi-real time) viscosity of the variable-viscosity mixture 538. In some embodiments, the calculated viscosity may affect the amount of time that is displayed on a timer of the display 540. In other embodiments, no timer is used (i.e., other indicia are used to identify the first time point and/or the second time point). While the description presented above focuses on input from temperature sensors, input from pressure sensors may be used in an analogous manner.

Figure 16:
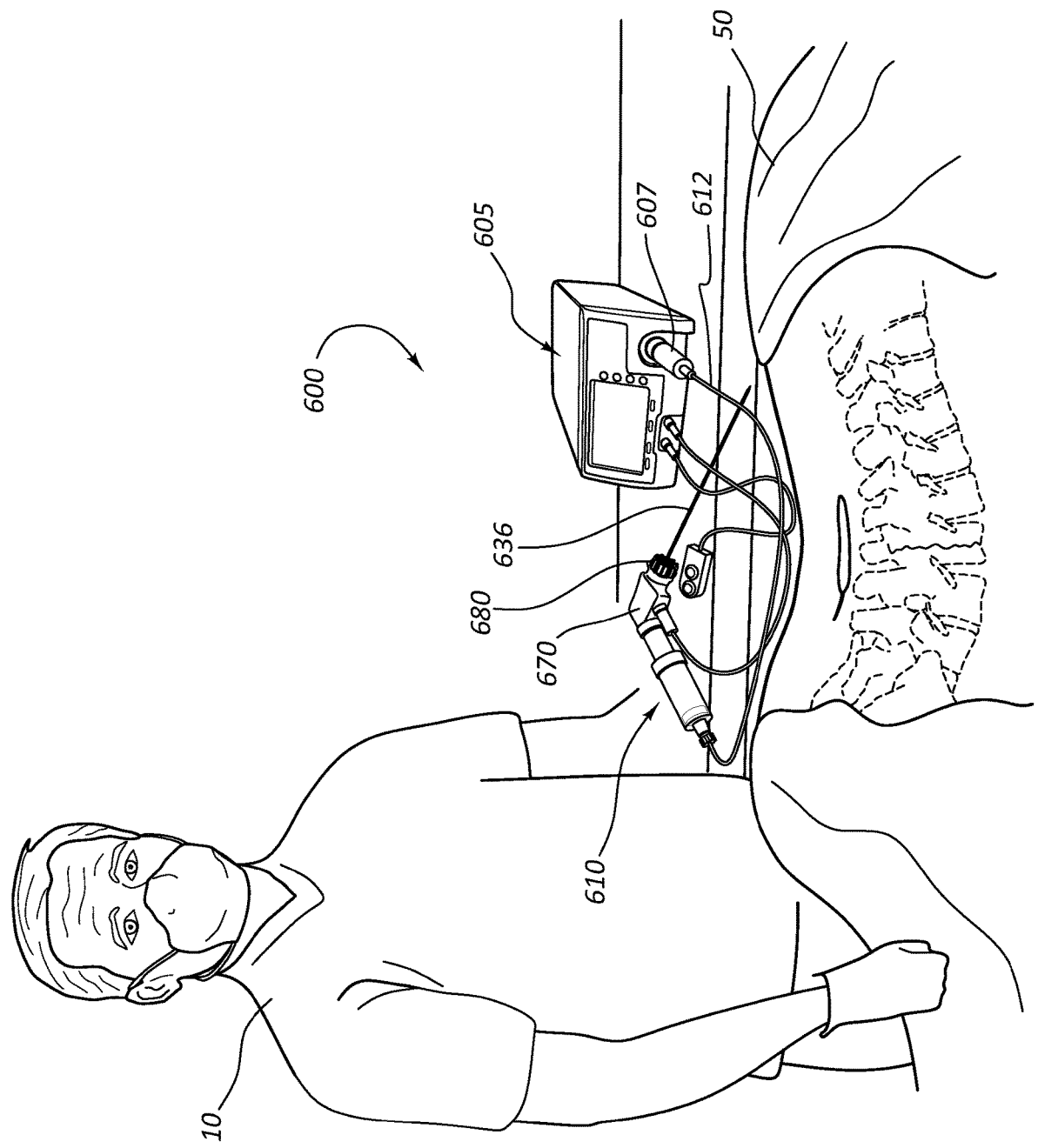
FIG. 16 is a perspective view of another system for delivering a variable-viscosity material to a patient.

FIG. 16 depicts another embodiment of a system for delivering a variable-viscosity mixture to a patient 50. As shown in FIG. 16, the system 600 includes a delivery device 610 and a control box 605. The control box 605 includes a hydraulic pump 607 that is configured to pump fluid from the control box 605 through tubing 612 to the delivery device 610. The fluid from the control box 605 may advance a mixture within the delivery device 610, thereby causing the mixture to pass through a cannula 636 and into a region of a vertebra of the patient. The mixture that is initially within the delivery device 610 may be a variable-viscosity mixture for delivery to a vertebra of the patient 50.

For example, during a kyphoplasty or vertebroplasty procedure, a practitioner 10 may cause the hydraulic pump 607 to deliver fluid through the tubing 612 to the delivery device 610, thereby pushing a variable-viscosity cement that is stored within the delivery device 610 through the cannula 636 and into a vertebra of the patient 50.

In some embodiments, the delivery device 610 comprises a radiofrequency energy delivery device 670 that is configured to deliver radiofrequency energy to the variable-viscosity mixture as it passes through the delivery device 610. The power for operating the radiofrequency energy delivery device 670 may be provided by the control box 605. For example, the practitioner 10 may operate an actuator 680 (e.g., a handheld actuator) such that, upon actuation, the control box 605 provides power to the radiofrequency delivery device 670. The radiofrequency energy from the radiofrequency delivery device 670 may cause the variable-viscosity mixture to increase in viscosity. In other words, the variable-viscosity mixture may be stored at a low viscosity within the delivery device 610 and then be converted to a relatively high viscosity mixture upon delivery of radiofrequency energy. A system 600 configured in this way may allow for ejection of cement over extended periods of time.

In some embodiments that use radiofrequency energy to alter the viscosity of a variable-viscosity mixture, a temperature sensor (e.g., a temperature sensor within the delivery device 610 just downstream of the radiofrequency energy delivery device 670) may be used in a manner analogous to that described above in connection with system 600. For example, a temperature sensor may be used to detect the temperature of the variable-viscosity mixture after it has been subjected to radiofrequency energy. Input from the temperature sensor may be relayed to the control box 605 or some other apparatus that analyzes (e.g., calculates or estimates) the viscosity and/or the rate of change in viscosity for the variable-viscosity mixture. Such information may be used to determine when indicia (e.g., indicia on a display) will change between states at a first time point and/or a second time point as described above. Other sensors (e.g., pressure sensors or sensors that detect the amount of material that remains within the delivery device 610) may be used in an analogous manner.

Numerous different types of indicia for alerting a practitioner of a boundary between a delivery period and a non-delivery period are within the scope of this disclosure. In some embodiments, one or more indicia for alerting a practitioner of a boundary between a delivery period and a non-delivery period include numeric indicia. In some embodiments, the one or more indicia include non-numeric indicia. In some embodiments, one or more indicia include audible indicia. In some embodiments, the one or more indicia include haptic indicia.

Particular examples of changes in indicia that are within the scope of this disclosure include (1) a count-down timer or a count-up timer that displays changes in time, (2) lights (e.g., LEDs) that change color, arrangement, and/or intensity (e.g., on or off), (3) audible alarms, and (4) haptic vibrations.

Various displays that may be used to display indicia are shown in FIGS. 17-19. For example, FIG. 17 depicts a tablet 785 that includes a display 740. In other embodiments, other suitable remote displays may be used, such as the display of a laptop. In the depicted embodiment, the display 740 includes a gauge 742 that is designed to indicate the viscosity of a variable-viscosity mixture. For example, the gauge 742 may indicate whether the variable-viscosity mixture is of insufficient viscosity, is of suitable viscosity, or is too viscous for injection into a patient.

The display 740 may also include various other indicia, such as indicia that provide one or more of the following: a digital readout of the viscosity of the variable-viscosity mixture, the pressure of the variable-viscosity mixture (or the pressure of a fluid used to displace the variable-viscosity mixture), the amount of time that has elapsed or the amount of time remaining before a boundary between a delivery period and a non-delivery period, a temperature measurement (e.g., of the variable-viscosity mixture or the ambient environment), and the amount of variable-viscosity mixture that remains for delivery.

FIG. 18 provides a view of a housing 890 that includes a display 840. In some embodiments, the housing 890 may be mechanically coupled (e.g., attached) to the injector of a delivery device in a manner similar to that shown in FIGS. 10-15. The display 840 of the housing 890 may display indicia that transition between states at a first time point and/or a second time point. For example, the display 840 may include three lights or other indicia 842, 843, 844. The first light or other indicium 842 may indicate to the practitioner that the variable-viscosity mixture is of insufficient viscosity for delivery to the patient. A second light or other indicium 843 may indicate to the practitioner that the variable-viscosity mixture is of suitable viscosity for delivery to a patient. A third light or other indicium 844 may indicate to the practitioner that the variable-viscosity mixture is too viscous for delivery to a patient. In some embodiments, as the visual indicia transition between states, an audible alarm may sound, thereby providing changes in both audible and visual indicia at the first time point and/or the second time point. By observing the indicia transitioning between the states, the practitioner may easily determine when to carry out particular steps of a procedure.

FIG. 19 provides a perspective view of a control box 905 having a display 940. In the depicted embodiment, the display 940 includes two indicia. The first indicium 945 is understood by the practitioner as indicating that the cement is of suitable viscosity for delivery to a patient. The second indicium 946 is understood by the practitioner as indicating that the cement may not be of suitable viscosity for delivery to the patient. By observing such transitions between these indicia, the practitioner may carry out steps of a procedure in an appropriate manner.

The sensors described herein may communicate with the displays in any suitable manner. For example, in some embodiments, a sensor is coupled to a transmitter. In some embodiments, the transmitter is configured to wirelessly transmit information from the sensor. For example, the transmitter may be configured as a Bluetooth transmitter and/or as a WiFi transmitter.

The transmitter may allow for wireless remote displays. The ability to have a remote display may provide a significant benefit to the practitioner. For instance, in many medical procedures, space in the immediate vicinity of the patient's body is at a premium, particularly the space near the incision site of a kyphoplasty or vertebroplasty procedure. When a delivery device is close to the incision site, a display mounted on the delivery device may obscure a user's view of the incision site and/or may block access to the incision site by surgical staff. Additionally, a display mounted on an inflation device may only be visible to the individual using the inflation device.

One benefit of the transmitter is that a signal from the sensor may be sent to a remote display device located in the operating room. The remote display device may then be placed away from the incision site, thereby allowing a user of the delivery device a clear view of the incision site. The remote display device may be located so as to not block access to the incision site by surgical staff. Also, the remote display device may be located so as to be clearly visible to other surgical staff. This may allow multiple individuals to be aware of the information provided on the display. This knowledge may in turn assist surgical staff to work as a team instead of waiting for instructions from the user of the inflation device.

Various variable-viscosity mixtures for use in the systems and methods described herein are within the scope of this disclosure. For example, in some embodiments, the variable-viscosity mixture is a cement that is suitable for stabilization of bone (e.g., a vertebra). In some embodiments, the cement includes polymethyl methacrylate. In some embodiments, the cement is a drug-eluting and/or a biologic-eluting cement.

Exemplary Embodiments

The following embodiments are illustrative and exemplary, and are not meant as a limitation of the scope of the present disclosure in any way.

I. Method for Providing Treatment to a Patient

In one embodiment, a method for providing treatment to a patient comprises initiating a pre-treatment timer on a timing mechanism, wherein the timing mechanism measures a pre-treatment procedure, and wherein the timing mechanism initiates a first alert at completion of the timing mechanism's pre-treatment measurement. The method may also comprise performing the pre-treatment procedure, and initiating a treatment timer on the timing mechanism, wherein the timing mechanism measures a treatment procedure, and wherein the timing mechanism initiates a second alert at completion of the timing mechanism's treatment measurement.

The pre-treatment procedure may comprise combining ingredients to be used during the treatment procedure.

The timing mechanism may be set to measure a specified amount of time to permit sufficient combination of the ingredients.

In some embodiments, measuring a pre-treatment procedure comprises counting down a specified amount of time.

In some embodiments, measuring a pre-treatment procedure comprises counting the time elapsed after initiating the pre-treatment timer.

In some embodiments, the pre-treatment procedure comprises accessing a part of a patient's body in preparation for the treatment procedure.

In some embodiments, the pre-treatment procedure comprises preparing surgical tools to be used in the treatment procedure.

In some embodiments, the pre-treatment procedure comprises delivery of anesthetics.

In some embodiments, initiating the pre-treatment timer on the timing mechanism comprises receiving an actuation force on a component of the timing mechanism.

In some embodiments, the first alert comprises one or more of a visual alert, an audible alert, and a haptic alert.

In some embodiments, initiating a treatment timer on the timing mechanism is an internal automatic procedure of the timing mechanism after completion of the pre-treatment measurement.

In some embodiments, the treatment procedure comprises repairing bone fractures.

In some embodiments, the treatment procedure comprises a kyphoplasty procedure.

In some embodiments, the treatment procedure comprises a vertebroplasty procedure.

In some embodiments, the treatment procedure comprises inflating an inflatable device during an angioplasty procedure.

In some embodiments, the mixture comprises a fluid material that cures into a solid material after injection into the patient.

In some embodiments, the mixture comprises a cement mixture that cures into a solid material after injection into a bone of the patient.

In some embodiments, the first pre-determined amount of time is input by a medical practitioner.

In some embodiments, the second predetermined amount of time is based on the amount of time for which the mixture maintains low enough viscosity to insert into the patient's body in the treatment procedure.

In some embodiments, the pre-treatment measurement is set to measure a time between one and a half minutes and two and a half minutes.

In some embodiments, the treatment measurement is set to measure a time between fifteen minutes and twenty-five minutes.

In some embodiments, the pre-treatment measurement is set to measure two minutes and the treatment measurement is set to measure twenty minutes.

In some embodiments, the timing mechanism is programmable.

II. Method of Treating a Vertebral Compression Fracture

One embodiment of a method for treating a vertebral compression fracture comprises initiating a pre-treatment timer on a timing mechanism, wherein the timing mechanism measures a first predetermined amount of time for completion of a pre-treatment procedure, wherein the timing mechanism initiates a first alert at completion of the first predetermined amount of time, and wherein after initiating the alert member, the timing mechanism automatically initiates a treatment timer on the timing mechanism, wherein the timing mechanism measures a second predetermined amount of time for completion of a treatment procedure, and wherein the timing mechanism initiates a second alert at completion of the second predetermined amount of time. The method may also comprise performing the pre-treatment procedure comprising combining ingredients for a mixture to be used in a treatment procedure for a patient, and permitting the ingredients to react with each other for the first predetermined amount of time. The method may also comprise performing the treatment procedure wherein the treatment procedure comprises use of the mixture in treating a patient.

In some embodiments, the timing mechanism is set to measure a specified amount of time to permit sufficient reaction of the ingredients.

In some embodiments, measuring a pre-treatment procedure comprises counting down a specified amount of time.

In some embodiments, measuring a pre-treatment procedure comprises counting the time elapsed after initiating the pre-treatment timer.

In some embodiments, the pre-treatment procedure comprises accessing a part of a patient's body in preparation for the treatment procedure.

In some embodiments, the pre-treatment procedure comprises preparing surgical tools to be used in the treatment procedure.

In some embodiments, the pre-treatment procedure comprises delivery of anesthetics.

In some embodiments, initiating the pre-treatment timer on the timing mechanism comprises receiving an actuation force on a component of the timing mechanism.

In some embodiments, the first alert comprises one or more of a visual alert, an audible alert, and a haptic alert.

In some embodiments, the second alert comprises one or more of a visual alert, an audible alert, and a haptic alert.

In some embodiments, initiating a treatment timer on the timing mechanism is an internal automatic procedure of the timing mechanism after completion of the pre-treatment measurement.

In some embodiments, the treatment procedure comprises a kyphoplasty procedure.

In some embodiments, the treatment procedure comprises a vertebroplasty procedure.

In some embodiments, the mixture comprises a fluid material that cures into a solid material after injection into the patient.

In some embodiments, the mixture comprises a cement mixture that cures into a solid material after injection into a bone of the patient.

In some embodiments, the first pre-determined amount of time is input by a medical practitioner.

In some embodiments, the second predetermined amount of time is based on the amount of time for which the mixture maintains low enough viscosity to insert into the patient's body in the treatment procedure.

In some embodiments, the pre-treatment measurement is set to measure a time between one and a half minutes and two and a half minutes.

In some embodiments, the treatment measurement is set to measure a time between twenty-five minutes and thirty-five minutes.

In some embodiments, the pre-treatment measurement is set to measure two minutes and the treatment measurement is set to measure twenty minutes.

In some embodiments, the timing mechanism is programmable.

III. Method of Performing an Endovascular Procedure on a Patient

One embodiment of a method for performing an endovascular procedure on a patient comprises providing a first input to initiate a treatment timer on a timing mechanism by exceeding a first pressure threshold in a lumen, wherein the treatment timer measures a predetermined amount of time for maintaining pressure above a second pressure threshold, wherein the timing mechanism initiates an alert at the predetermined amount of time. The method for performing an endovascular procedure on a patient may further comprise providing a second input to stop the treatment timer, wherein the second input comprises reducing the pressure in the lumen to a level below a third pressure threshold.

In some embodiments, the first input is provided by a pressure device comprising a plunger and a cylinder.

In some embodiments, the lumen is defined by a surgical tube.

In some embodiments, the timing mechanism comprises a display.

In some embodiments, the display conveys information relating to one or more of a pressure reading, time elapsed after initiation of a timer, and time remaining until an alert is initiated.

Some embodiments further comprise maintaining a pressure in the lumen that exceeds the second pressure threshold during a portion of the procedure.

In some embodiments, the first pressure threshold, the second pressure threshold, and the third pressure threshold are all distinct from each other.

In some embodiments, the procedure is angioplasty.

Some embodiments further comprise inflating a medical device.

Some embodiments further comprise positioning the medical device in a body lumen of a patient before inflation.

In some embodiments, the treatment timer counts down a time for which it is safe to maintain inflation of the inflatable device within the body lumen.

IV. Method for Timing a Treatment to a Patient

One embodiment of a method for timing a treatment to a patient comprises receiving input at a timing mechanism to initiate a pre-treatment timer on the timing mechanism, wherein the timing mechanism measures a pre-treatment procedure, and wherein the timing mechanism initiates a first alert at completion of the timing mechanism's pre-treatment measurement; and initiating a treatment timer on the timing mechanism, wherein the timing mechanism measures a treatment procedure, and wherein the timing mechanism initiates a second alert at completion of the timing mechanism's treatment measurement.

In some embodiments, the pre-treatment procedure comprises combining ingredients to be used during the treatment procedure.

In some embodiments, the timing mechanism is set to measure a specified amount of time to permit sufficient combination of the ingredients.

In some embodiments, measuring the pre-treatment procedure comprises counting down a specified amount of time.

In some embodiments, measuring a pre-treatment procedure comprises counting the time elapsed after initiating the pre-treatment timer.

In some embodiments, the pre-treatment procedure comprises accessing a part of a patient's body in preparation for the treatment procedure.

In some embodiments, the pre-treatment procedure comprises preparing surgical tools to be used in the treatment procedure.

In some embodiments, the pre-treatment procedure comprises delivery of anesthetics.

In some embodiments, initiating the pre-treatment timer on the timing mechanism comprises receiving an actuation force on a component of the timing mechanism.

In some embodiments, the first alert comprises one or more of a visual alert, an audible alert, and a haptic alert.

In some embodiments, the second alert comprises one or more of a visual alert, an audible alert, and a haptic alert.

In some embodiments, initiating a treatment timer on the timing mechanism is an internal automatic procedure of the timing mechanism after completion of the pre-treatment measurement.

In some embodiments, the treatment procedure comprises repairing bone fractures.

In some embodiments, the treatment procedure comprises a kyphoplasty procedure.

In some embodiments, the treatment procedure comprises a vertebroplasty procedure.

In some embodiments, the treatment procedure comprises inflating an inflatable device during an angioplasty procedure.

In some embodiments, the mixture comprises a fluid material that cures into a solid material after injection into the patient.

In some embodiments, the mixture comprises a cement mixture that cures into a solid material after injection into a bone of the patient.

In some embodiments, the first pre-determined amount of time is input by a medical practitioner.

In some embodiments, the second predetermined amount of time is based on the amount of time for which the mixture maintains low enough viscosity to insert into the patient's body in the treatment procedure.

In some embodiments, the pre-treatment measurement is set to measure a time between one and a half minutes and two and a half minutes.

In some embodiments, the treatment measurement is set to measure a time between fifteen minutes and twenty-five minutes.

In some embodiments, the pre-treatment measurement is set to measure two minutes and the treatment measurement is set to measure twenty minutes.

In some embodiments, the timing mechanism is programmable.

V. System for Delivering a Mixture to a Patient

In one embodiment, a system for delivering a mixture to a patient comprises a delivery device that is configured to deliver a variable-viscosity mixture to a patient, and one or more indicia that are configured to automatically transition from a first state to a second state, and then to a third state, wherein the transition to the second state occurs at a first time point and the transition to the third state occurs at the second time point, wherein the transition from the first state to the second state at the first time point indicates a boundary between a first non-delivery period and a delivery period, and wherein the transition to the third state at the second time point indicates a boundary between the delivery period and a second non-delivery period.

In some embodiments, the system further comprises a timer, wherein the length of one or both of the first non-delivery period and the delivery period are fixed periods of time that are programmed into the timer.

In some embodiments, the system further comprises a sensor, wherein the second time point is determined, at least in part, by input from the sensor.

In some embodiments, the sensor is a temperature sensor.

In some embodiments, the temperature sensor is configured to sense a temperature of the variable-viscosity mixture when the variable-viscosity mixture is disposed within the delivery device.

In some embodiments, the temperature sensor is configured to sense ambient temperature.

In some embodiments, the first time point is determined, at least in part, by input from the temperature sensor.

In some embodiments, the one or more indicia comprise one or more visible indicia.

In some embodiments, the one or more indicia comprise one or more audible indicia.

In some embodiments, the one or more indicia comprise one or more haptic indicia.

In some embodiments, the system further comprises a display screen.

In some embodiments, the display screen is configured to display the viscosity of the variable-viscosity mixture.

In some embodiments, the display screen is mechanically coupled to the delivery device.

In some embodiments, the display screen is a remote display screen that is in wireless communication with the delivery device.

In some embodiments, the delivery device comprises an injector.

In some embodiments, the system further comprises a radiofrequency delivery device, wherein the radiofrequency delivery device is configured to deliver radiofrequency energy to the variable-viscosity mixture.

In some embodiments, the system further comprises a plurality of substances that, when combined, form the variable-viscosity mixture, wherein the variable-viscosity mixture is a cement suitable for injection into a vertebra of a patient.

VI. Methods for Delivering a Mixture to a Patient

In one embodiment, a method of delivering a mixture to a patient comprises obtaining a variable-viscosity mixture, and delivering the variable-viscosity mixture from a delivery device to a patient, wherein the variable-viscosity mixture is delivered from the delivery device within a period of time between a first time point and a second time point; wherein one or more indicia transition from a first state to a second state and then to a third state, wherein the transition to the second state occurs at the first time point, and the transition to the third state occurs at the second time point; wherein the first time point indicates a boundary between a first non-delivery period and a delivery period; and wherein the second time point indicates a boundary between the delivery period and a second non-delivery period.

In some embodiments, the second time point is determined, at least in part, by input from a sensor.

In some embodiments, the first time point is determined, at least in part, by input from the sensor.

In some embodiments, the variable-viscosity mixture is a cement.

In some embodiments, the cement comprises polymethyl methacrylate.

In some embodiments, delivery of the variable-viscosity mixture to the patient comprises delivery of the variable-viscosity mixture into a region within a vertebra of a patient.

In some embodiments, the sensor is a temperature sensor and the input is a temperature measurement.

In some embodiments, the temperature sensor senses temperature of the variable-viscosity mixture.

In some embodiments, the temperature sensor senses ambient temperature.

In some embodiments, obtaining the variable-viscosity mixture comprises mixing two or more substances.

In some embodiments, the delivery device comprises an injector.

In some embodiments, the one or more indicia comprise one or more visible indicia.

In some embodiments, the one or more indicia comprise one or more audible indicia.

In some embodiments, the one or more indicia comprise one or more haptic indicia.

In some embodiments, the method further comprises viewing a display screen that displays the one or more indicia in order to identify both when the transition to the second state occurs and when the transition to the third state occurs.

In some embodiments, the display screen is configured to display the viscosity of the variable-viscosity mixture.

In some embodiments, the display screen is mechanically coupled to the delivery device.

In some embodiments, the display screen is a remote display screen.

In some embodiments, the remote display is in wireless communication with the delivery device.

In some embodiments, the display screen is configured to display both numeric and non-numeric indicia.

In some embodiments, the display screen is configured to display a temperature.

In some embodiments, the display screen is configured to display one or more of a count-down timer or a count-up timer.

In some embodiments, the method further comprises delivering radiofrequency energy to the variable-viscosity mixture as the variable-viscosity mixture is ejected from the delivery device.

In some embodiments, the method further comprises measuring a pressure within a chamber of the delivery device.

In some embodiments, the method further comprises sensing the amount of variable-viscosity mixture in a chamber of the delivery device.

In some embodiments, the method further comprises sensing the temperature of the variable-viscosity mixture as it is ejected from the delivery device.

VII. Kit for Delivering a Variable-Viscosity Mixture to a Patient

In one embodiment, a kit for delivering a variable-viscosity mixture to a patient comprises a first substance and a second substance, wherein the first substance and the second substance, when mixed together, form a variable-viscosity cement for stabilizing a vertebra of a patient; a delivery device for delivering the variable-viscosity cement to the vertebra of the patient; a temperature sensor; and a display, wherein the display is configured to display indicia that change states at a first time point and a second time point based at least in part on input from the temperature sensor.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified.

Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A system for delivering a mixture to a patient, the system comprising:
   a delivery device configured to deliver a variable-viscosity mixture to a patient;
   one or more indicia that are configured to automatically transition from a first state to a second state, and then to a third state,
   a timing mechanism;
   a temperature sensor configured to sense an ambient temperature,
   wherein the transition to the second state occurs at a first time point and the transition to the third state occurs at a second time point,
   wherein the transition from the first state to the second state at the first time point indicates a boundary between a first non-delivery period and a delivery period and indicates a start of the delivery period,
   wherein the transition from the second state to the third state at the second time point indicates a boundary between the delivery period and a second non-delivery period and indicates a start of the second non-delivery period,
   wherein the first non-delivery period is a set time interval, and
   wherein the timing mechanism comprises:
      a first timer configured to time the first non-delivery period, and
      a second timer configured to time the delivery period,
   wherein the timing mechanism automatically activates the second timer at the end of the first non-delivery period; and
   a volume sensor configured to detect a delivered volume of the variable-viscosity mixture,
   wherein a duration of the delivery period is determined by detecting the delivered volume of the variable-viscosity mixture.

2. The system of claim 1, wherein the temperature sensor is configured to sense a temperature of the variable-viscosity mixture when the variable-viscosity mixture is disposed within the delivery device.

3. The system of claim 2, wherein the temperature sensor is configured to sense the temperature of the variable-viscosity mixture as it is ejected from the delivery device.

4. The system of claim 1, wherein the first time point is determined, at least in part, by input from the temperature sensor.

5. The system of claim 1, further comprising a display screen.

6. The system of claim 5, wherein the display screen is configured to display the viscosity of the variable-viscosity mixture.

7. The system of claim 5, wherein the display screen is mechanically coupled to the delivery device.

8. The system of claim 5, wherein the display screen is a remote display screen that is in wireless communication with the delivery device.

9. The system of claim 1, further comprising a radiofrequency delivery device, wherein the radiofrequency delivery device is configured to delivery radiofrequency energy to the variable-viscosity mixture.

10. The system of claim 1, further comprising a plurality of substances that, when combined, form the variable-viscosity mixture, wherein the variable-viscosity mixture is a cement suitable for injection into a vertebra of the patient.

11. The system of claim 1, further comprising a pressure sensor.

12. The system of claim 11, further comprising one or more chambers configured to house at least one of the variable-viscosity mixture and the fluid material.

13. The system of claim 12, wherein the pressure sensor is configured to sense the pressure within at least one of the one or more chambers.

14. The system of claim 1, further comprising a fluid material coupled to the variable-viscosity mixture such that a pressure of the fluid material corresponds to a pressure of the variable-viscosity mixture.

15. The system of claim 14, wherein displacement of the variable-viscosity mixture corresponds to displacement of the fluid material.

16. The system of claim 1, wherein an input from the volume sensor is utilized to determine the first time point.

17. The system of claim 1, wherein an input from the volume sensor is utilized to determine the second time point.

* * * * *